(12) United States Patent
Yamada et al.

(10) Patent No.: US 9,250,165 B2
(45) Date of Patent: Feb. 2, 2016

(54) SMEAR STAINING APPARATUS, SMEAR PREPARING APPARATUS, SMEAR PROCESSING SYSTEM, AND METHOD FOR DETERMINING STAINING CONDITION

(75) Inventors: Kazuhiro Yamada, Kobe (JP); Mitsuo Yamasaki, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 13/044,145

(22) Filed: Mar. 9, 2011

(65) Prior Publication Data
US 2011/0223632 A1 Sep. 15, 2011

(30) Foreign Application Priority Data
Mar. 11, 2010 (JP) ................................. 2010-054265

(51) Int. Cl.
| | | |
|---|---|---|
| *G06F 19/00* | (2011.01) | |
| *G06K 9/36* | (2006.01) | |
| *G01N 1/31* | (2006.01) | |
| *G01N 35/10* | (2006.01) | |

(52) U.S. Cl.
CPC ............ *G01N 1/312* (2013.01); *G01N 35/1016* (2013.01)

(58) Field of Classification Search
None
See application file for complete search history.

(56) References Cited

U.S. PATENT DOCUMENTS

| | | | |
|---|---|---|---|
| 5,671,288 A * | 9/1997 | Wilhelm et al. | 382/128 |
| 6,268,208 B1 | 7/2001 | Kondo | |
| 6,495,106 B1 * | 12/2002 | Kalra et al. | 422/510 |
| 6,800,249 B2 * | 10/2004 | de la Torre-Bueno | 422/63 |
| 7,297,311 B2 | 11/2007 | Tamura et al. | |
| 7,368,080 B2 | 5/2008 | Tamura et al. | |
| 2007/0010912 A1 * | 1/2007 | Feingold et al. | 700/245 |
| 2009/0239257 A1 * | 9/2009 | Levine et al. | 435/34 |

FOREIGN PATENT DOCUMENTS

| | | |
|---|---|---|
| JP | H04-291157 | 10/1992 |
| JP | 2001-021468 A | 1/2001 |
| JP | 2006-38781 | 2/2006 |
| WO | WO 9713135 * | 4/1997 |

OTHER PUBLICATIONS

Johansson et al. (The Journal of Histochemistry and Cytochemistry (2001) vol. 49:1073-1079).*

* cited by examiner

*Primary Examiner* — Lori A Clow
(74) *Attorney, Agent, or Firm* — Sughrue Mion, PLLC

(57) ABSTRACT

A smear staining apparatus comprising: a staining section which stains a smear sample with a quantity of stain fluid; and a controller, wherein the controller: receives information regarding a stain state on a smear sample which is stained according to a first staining condition by the staining section; and determines a second staining condition on the basis of the information and a target value which defines a targeted stain state, is disclosed. A smear preparing apparatus, a smear processing system and method for determining staining condition are also disclosed.

24 Claims, 16 Drawing Sheets

SMEAR STAINING APPARATUS, SMEAR PREPARING APPARATUS, SMEAR PROCESSING SYSTEM, AND METHOD FOR DETERMINING STAINING CONDITION

FIELD OF THE INVENTION

The present invention relates to a smear staining apparatus for staining a smear sample in which a sample such as blood is applied on a slide glass, a smear preparing apparatus, a smear processing system, and a method for determining the staining condition in staining the smear sample.

BACKGROUND

A smear staining apparatus for staining a smear sample is conventionally known (e.g., Japanese laid open patent application No. 2001-021468).

Japanese laid open patent application No. 2001-021468 discloses a smear staining apparatus for staining a smear sample by immersing the smear sample in a stain fluid bath. In the smear staining apparatus disclosed in this reference, the immersing time is determined by the user so as to stain the sample to a desired density.

The concentration of the concentrated stain fluid differs depending on the manufacturer and the manufacturing lot. Thus, an appropriate stain state may not necessarily be obtained after the concentrated stain fluid is replaced even if a constant immersing time is set. The immersing time thus needs to be re-determined if the concentrated stain fluid is replaced. However, although the operator determines the immersing time in the smear staining apparatus disclosed in the above document, the appropriate immersing time may not be determined at one time. Thus, the immersing time needs to be re-determined over and over until an appropriate stain state is obtained, which is a great load on the operator.

In view of the above situations, it is a main object of the present invention to provide a smear staining apparatus, a smear preparing apparatus, a smear processing system, and a method for determining the staining condition capable of easily determining an appropriate staining condition.

SUMMARY OF THE PRESENT INVENTION

A first aspect of the present invention is a smear staining apparatus comprising: a staining section which stains a smear sample with a quantity of stain fluid; and a controller, wherein the controller: receives information regarding a stain state on a smear sample which is stained according to a first staining condition by the staining section; and determines a second staining condition on the basis of the information and a target value which defines a targeted stain state.

A second aspect of the present invention is a smear preparing apparatus comprising: a smear preparing section for preparing a smear sample by smearing a sample on a slide glass; a staining section for staining the smear sample prepared by the smear preparing section using a quantity of stain fluid; and a controller, wherein the controller: receives information regarding a stain state on a smear sample which is stained according to a first staining condition by the staining section; and determines a second staining condition on the basis of the information and a target value which defines a targeted stain state.

A third aspect of the present invention is a smear processing system comprising: the smear staining apparatus of first aspect; and a smear imaging apparatus for imaging the smear sample stained by the smear staining apparatus to acquire an image, analyzing the obtained image, and outputting information regarding a stain state of the smear sample.

A fourth aspect of the present invention is a method of determining a staining condition including steps of: staining a smear sample according to a first staining condition by a staining apparatus for staining a smear sample using a quantity of stain fluid; acquiring information regarding a stain state of the smear sample stained by the staining apparatus according to the first staining condition from a smear imaging apparatus for imaging the stained smear sample and outputting information regarding the stain state; and determining a second staining condition of the staining apparatus based on the obtained information and a target value which defines a targeted stain state.

DETAILED DESCRIPTION OF THE PREFERRED EMBODIMENTS

The preferred embodiment of the present invention will now be described with reference to the drawings.

[Configuration of Smear Processing System]

Figure 1:
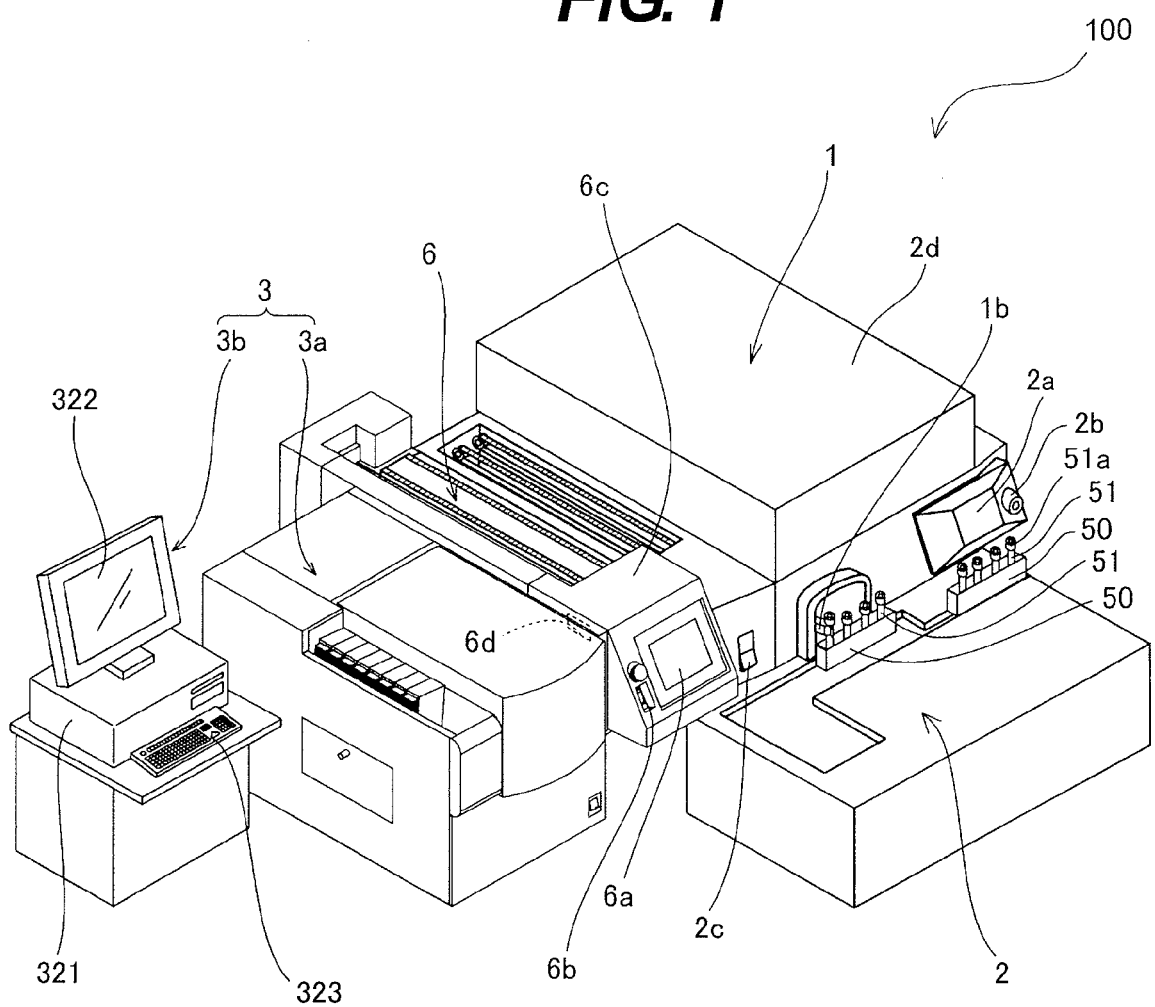
FIG. 1 is a perspective view showing an overall configuration of a smear processing system according to the embodiment.

FIG. 1 is a perspective view showing an overall configuration of a smear processing system according to the present embodiment. As shown in FIG. 1, a smear processing system 100 includes a blood smear preparing apparatus 1 and a sample imaging apparatus 3. A transport device 2 for transporting a blood sample accommodated in a test tube is arranged on the front side of the blood smear preparing apparatus 1, where the sample is transported to the blood smear preparing apparatus 1 by the transport device 2 so that the blood smear preparing apparatus 1 uses the relevant sample to prepare a smear sample. The prepared smear sample is imaged by the sample imaging apparatus 3, and the blood cells are classified through image processing.

<Configuration of Blood Smear Preparing Apparatus>

Figure 2:
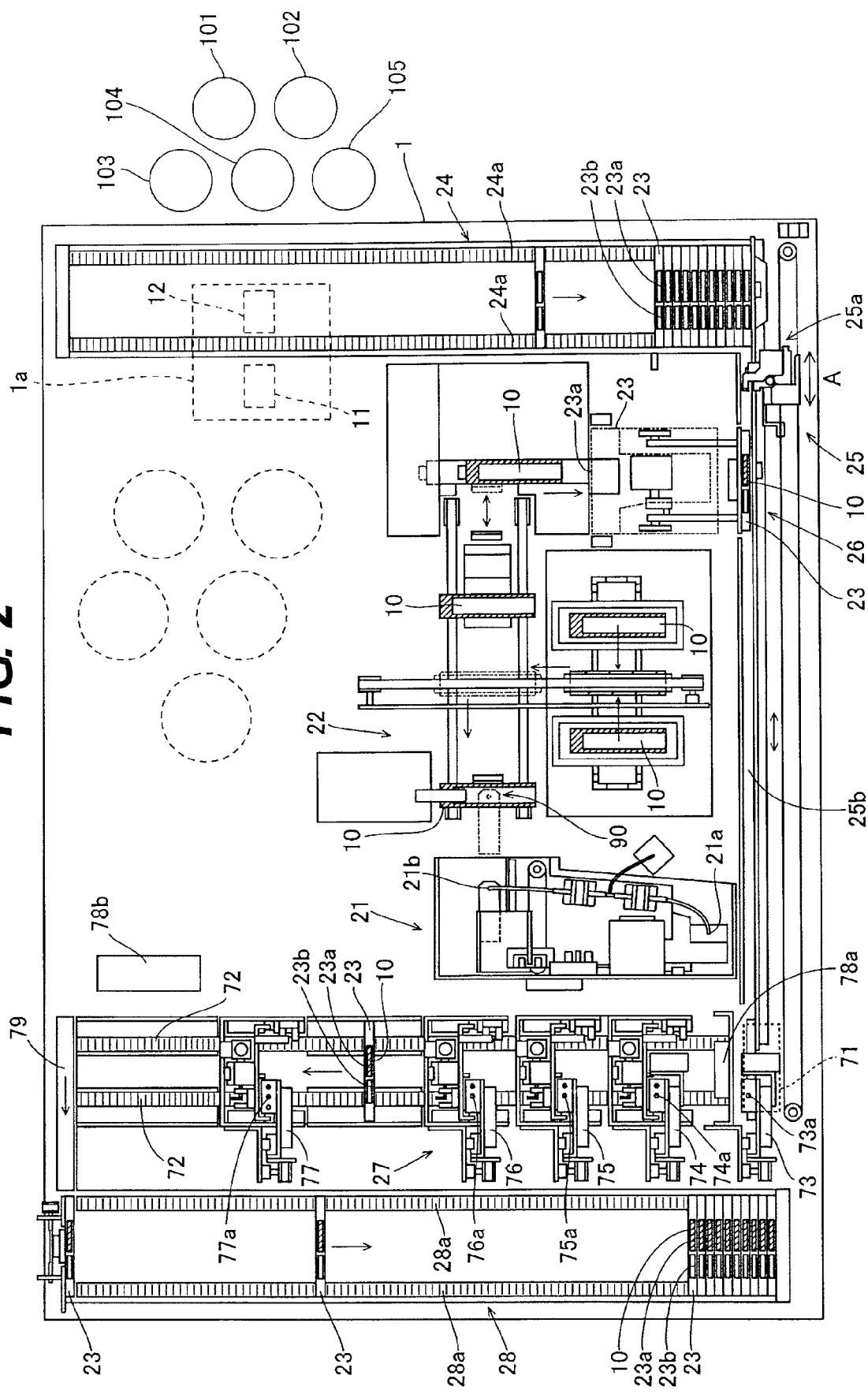
FIG. 2 is a plan view showing an internal structure of the blood smear preparing apparatus according to the embodiment.

The blood smear preparing apparatus 1 aspirates a blood sample and drops it on a slide glass, thinly stretches the blood sample on the slide glass and dries to prepare the smear sample, and then supplies the stain fluid to the smear sample to stain the blood on the slide glass. FIG. 2 is a plan view showing an internal structure of the blood smear preparing apparatus shown in FIG. 1. The blood smear preparing apparatus 1 is connected with five containers 101 to 105 in which the fluid to be used in the staining process are accommodated. In the present embodiment, May-Grunwald stain solution (concentrated stain fluid), diluted solution (phosphate buffer solution in the present embodiment), Giemsa solution (concentrated stain fluid), methanol solution, and sample cleaning solution are accommodated in the containers 101 to 105, respectively.

A shown in FIG. 2, the blood smear preparing apparatus 1 includes a control unit 1a having a function of controlling the operation for preparing the smear sample of the blood sample. The control unit 1a includes a CPU 11 and a memory 12 consisting of a ROM and a RAM. As shown in FIG. 1, the blood smear preparing apparatus 1 includes a display operation unit 2a including a touch panel, an activation switch 2b, a power switch 2c, and a cover 2d. The control unit 1a displays various types of information on the display operation unit 2a. The transport device 2 is arranged to automatically transport a sample rack 50 accommodating a test tube 51 accommodating the blood to the blood smear preparing apparatus 1.

The overall configuration of the blood smear preparing apparatus 1 will now be described. First, as shown in FIG. 1, the blood smear preparing apparatus 1 includes a hand member 1b for transporting the test tube 51 accommodating the blood from the transport device 2 side to the blood smear preparing apparatus 1 side. As shown in FIG. 2, the blood smear preparing apparatus 1 includes an aspirating and dispensing mechanism section 21, a smearing section 22, a resin cassette 23, a cassette accommodating section 24, a cassette transporting section 25, a slide glass inserting section 26, a staining section 27, and a storage section 28.

The aspirating and dispensing mechanism section 21 has a function of aspirating the blood from the test tube 51 transported to the blood smear preparing apparatus 1 side by the hand member 1b (see FIG. 1) and dropping the aspirated blood on a slide glass 10. As shown in FIG. 2, the aspirating and dispensing mechanism section 21 includes a piazza (aspiration needle) 21a for aspirating the blood from the test tube 51, and a dispensing pipette 21b for dispensing the aspirated blood on the slide glass 10.

Figure 3:
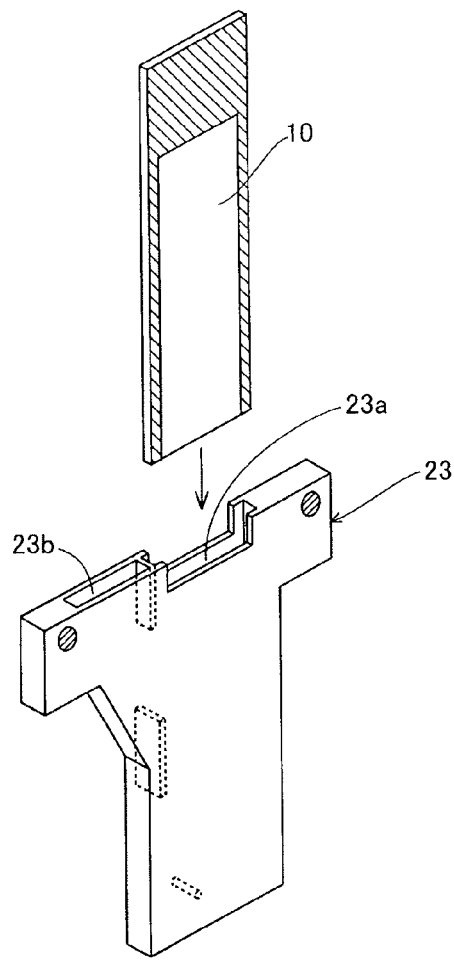
FIG. 3 is a perspective view showing the cassette and the slide glass used in the blood smear preparing apparatus according to the embodiment.
Figure 4:
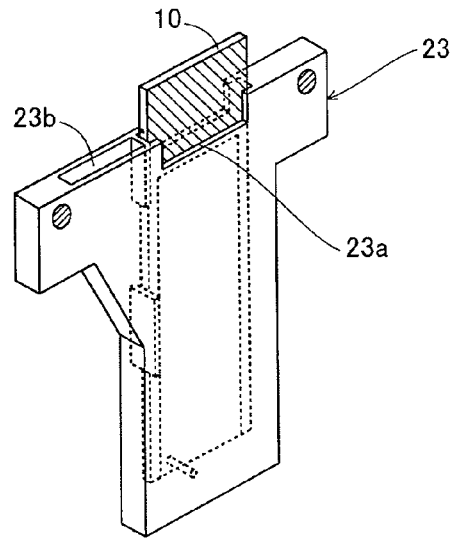
FIG. 4 is a perspective view showing the cassette and the slide glass used in the blood smear preparing apparatus according to the embodiment.

As shown in FIG. 2, the smearing section 22 is arranged to supply the slide glass 10 to a dispensing/smearing position 90, and to smear and dry the blood dropped on the slide glass 10 and print on the slide glass 10. The resin cassette 23 is configured so as to be able to accommodate the smeared slide glass 10 and the liquid to be used in the staining step. FIG. 3 and FIG. 4 are perspective views showing the cassette and the slide glass used in the blood smear preparing apparatus shown in FIG. 2. As shown in FIG. 3 and FIG. 4, the cassette 23 includes a slide glass accommodating hole 23a and a stain fluid aspirating and dispensing hole 23b. The slide glass accommodating hole 23a and the stain fluid aspirating and dispensing hole 23b are connected inside.

Furthermore, as shown in FIG. 2, the cassette accommodating section 24 is arranged to convey the cassette 23 into the cassette transporting section 25, and includes a feed belt 24a. The cassette transporting section 25 is arranged to transport the cassette 23 conveyed in from the cassette accommodating section 24 to the slide glass inserting section 26 and the staining section 27. As shown in FIG. 2, the cassette transporting section 25 includes a cassette transporting member 25a movable in a horizontal direction (A direction in FIG. 2), and a transport path 25b for transporting the cassette 23 supplied from the cassette accommodating section 24. As shown in FIG. 2, the slide glass inserting section 26 is arranged to accommodate the slid glass 10 performed with smearing and printing in the slide glass accommodating hole 23a of the cassette 23.

As shown in FIG. 2, the staining section 27 according to the present embodiment is arranged to perform supply and discharge of the stain fluid and the cleaning solution to the stain fluid aspirating and dispensing hole 23b of the cassette 23 transported by the cassette transporting member 25a, and to lift up and dry the slide glass 10 accommodated in the cassette 23 to perform the staining process on the smeared slide glass 10. The staining section 27 includes a sending member 71 for sending the cassette 23 transported by the cassette transporting member 25a to the staining section 27, a transport belt 72 for transporting the cassette 23 sent from the sending member 71, first to fifth aspirating and discharging units 73 to 77 for performing supply and discharge of the stain fluid and the cleaning solution to the cassette 23, a fan 78a for drying the slide glass 10 at the second aspirating and discharging unit 74, a fan 78b for drying the stained slide glass 10, and a send-out mechanism 79 for sending out the cassette 23 from the transport belt 72 to the transport belt 28a side of the storage section 28.

Figure 5:
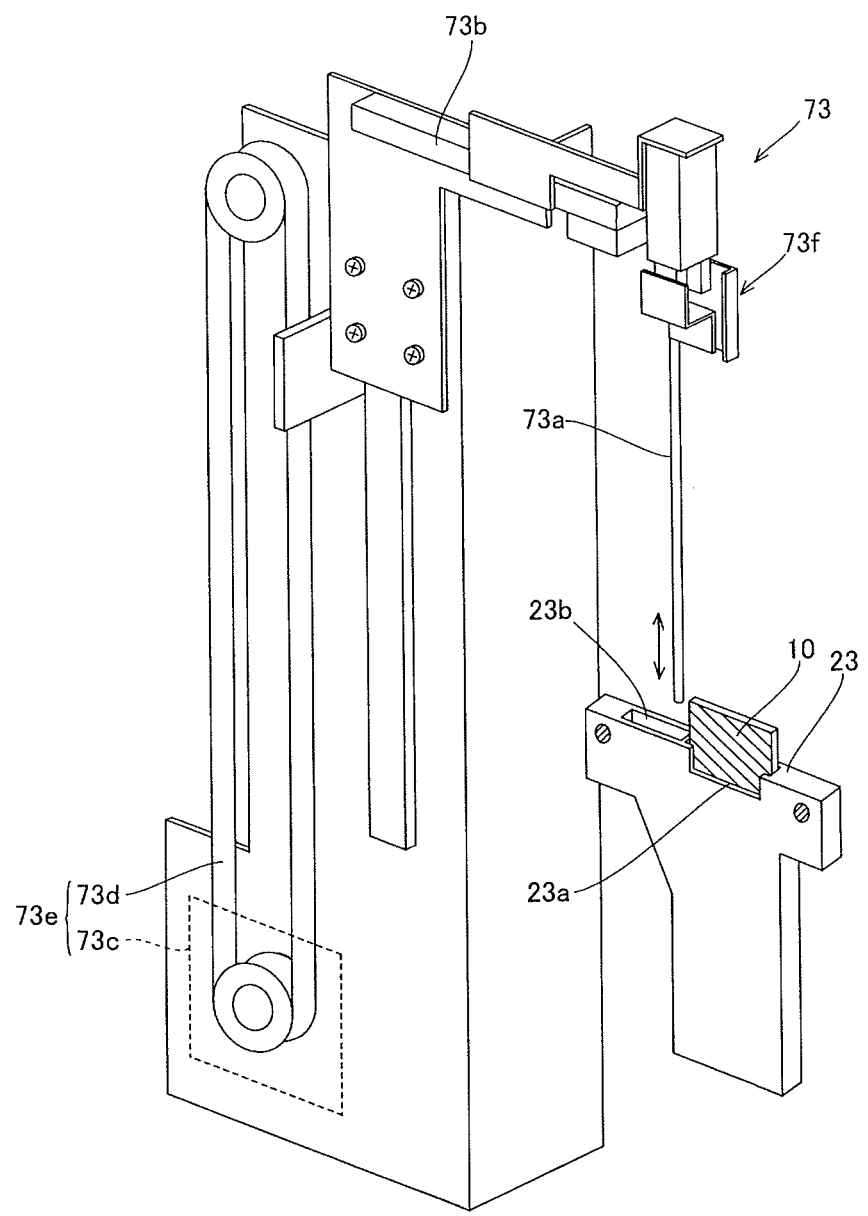
FIG. 5 is a perspective view showing a first aspirating and discharging unit of the staining section of the blood smear preparing apparatus according to the embodiment.

The first aspirating and discharging unit 73 will now be described. FIG. 5 is a perspective view showing a first aspirating and discharging unit of the staining section of the blood smear preparing apparatus shown in FIG. 2. As shown in FIG. 5, the first aspirating and discharging unit 73 includes a pipette 73a for supplying the methanol solution to the cassette 23, a pipette supporting member 73b for supporting the pipette 73a, and a drive mechanism 73e with a motor 73c and a drive belt 73d for moving the pipette supporting member 73b in the up and down direction. The relevant first aspirating and discharging unit 73 is configured to move the pipette 73a downward by the drive mechanism 73e to insert into the cassette 23, and supply the methanol solution. The pipette supporting member 73b of the first aspirating and discharging unit 73 is attached with a slide glass gripping member 73f for gripping and lifting up the slide glass 10 from the cassette 23.

The second aspirating and discharging unit 74 basically has a structure similar to the first aspirating and discharging unit 73. The third aspirating and discharging unit 75 to the fifth aspirating and discharging unit 77 have a structure in which the slide glass gripping member 73f is removed from the first aspirating and discharging unit 73. As shown in FIG. 2, the second aspirating and discharging 74 to the fifth aspirating and discharging unit 77 respectively includes a pipette 74a, 75a, 76a, and 77a for supplying May-Grunwald solution, May-Grunwald diluted solution, Giemsa diluted solution, and cleaning solution to the cassette 23. The pipette 74a is also used to aspirate (discharge) the methanol solution supplied by the pipette 73a from the cassette 23. Similarly, the pipette 75a is used to aspirate (discharge) the May-Grunwald solution supplied by the pipette 74a from the cassette 23, the pipette 76a is used to aspirate (discharge) the May-Grunwald diluted solution supplied by the pipette 75a from the cassette 23, and the pipette 77a is used to aspirate (discharge) the Giemsa diluted solution supplied by the pipette 76a from the cassette 23.

Figure 6:
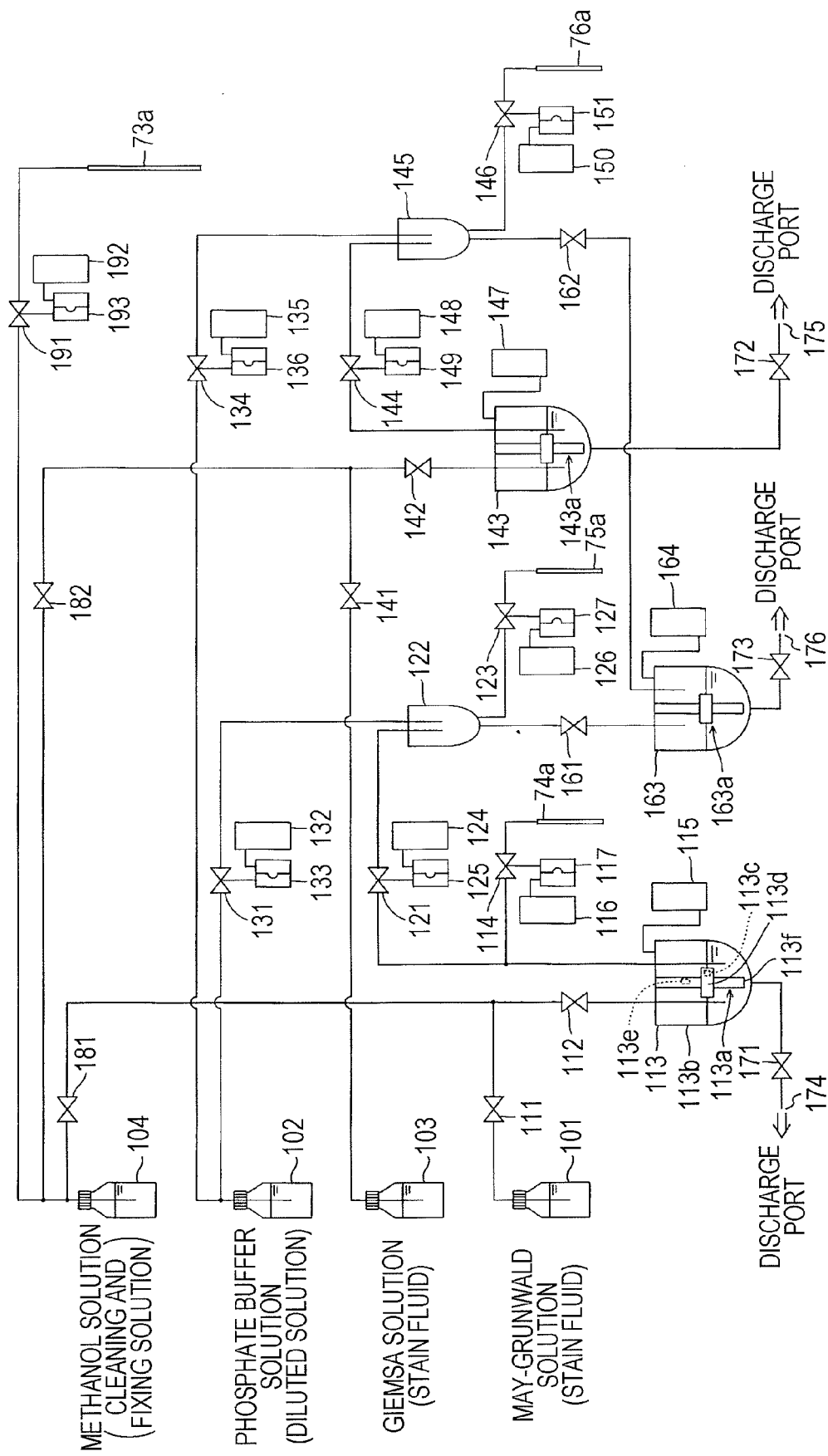
FIG. 6 is a fluid circuit diagram showing the supply path of the liquid supplied to the staining section of the blood smear preparing apparatus according to the embodiment.

The supply path of the liquid supplied from each pipette 73a, 74a, 75a, and 76a of the first aspirating and discharging unit 73 to the fourth aspirating and discharging unit 76 of the staining section 27 according to the present embodiment will now be described in detail. FIG. 6 is a fluid circuit diagram showing the supply path of the liquid supplied to the staining section shown in FIG. 2. As shown in FIG. 6, four containers 101 to 104 for accommodating the liquid to be supplied to the staining section are arranged on the supply path according to the present embodiment. Specifically, May-Grunwald solution serving as the concentrated stain fluid is accommodated in the container 101, the diluted solution (phosphate buffer solution) is accommodated in the container 102, the Giemsa solution serving as the concentrated stain fluid is accommodated in the container 103, and the methanol solution is accommodated in the container 104.

As shown in FIG. 6, the container 101 accommodating the May-Grunwald solution serving as the concentrated stain fluid is connected to the pipette 74a of the second aspirating and discharging unit 74 through a valve 111, a valve 112, a chamber 113, and a valve 114. An air pressure adjustor 115 is connected to the chamber 113. The valve 114 is connected to a diaphragm pump 117 connected to an air pressure adjustor 116.

The chamber 113 is arranged on the lower side of the blood smear preparing apparatus 1 (not shown). As shown in FIG. 6, the chamber 113 is configured by a tank 113b interiorly including a float switch 113a. When the liquid in the tank 113b reaches a defined amount, the float switch 113a detects the same. The air pressure adjustor 115 has a function of pressurizing and depressurizing the interior of the chamber 113, to which the air pressure adjustor 115 is connected. The diaphragm pump 117 has a function of aspirating and discharging a constant amount of solution. A plurality of air pressure adjustors and diaphragm pumps installed in the fluid path according to the present embodiment have functions similar to the air pressure adjustor 115 and the diaphragm pump 117.

The container 101 is also connected to the pipette 75a of the third aspirating and discharging unit 75 through the valve 111, the valve 112, the chamber 113, a valve 121, and a mixed chamber 122, and a valve 123. The valve 121 is connected with a diaphragm pump 125 connected to an air pressure adjustor 124. The valve 123 is connected to a diaphragm pump 127 connected to an air pressure adjustor 126. The container 102 accommodating the diluted solution (phosphate buffer solution) is connected to the mixed chamber 122 through a valve 131. The valve 131 is connected with a diaphragm pump 133 connected to an air pressure adjustor 132. The mixed chamber 122 is arranged to mix the May-Grunwald solution or the concentrated stain fluid accommodated in the container 101 and the diluted solution (phosphate buffer solution) accommodated in the container 102.

The container 103 accommodating the Giemsa solution serving as the concentrated stain fluid is connected to the pipette 76a of the fourth aspirating and discharging unit 76 through a valve 141, a valve 142, a chamber 143, a valve 144, a mixed chamber 145, and a valve 146. An air pressure adjustor 147 is connected to the chamber 143. The valve 144 is connected to a diaphragm pump 149 connected to an air pressure adjustor 148. The valve 146 is connected to a diaphragm pump 151 connected to an air pressure adjustor 150. The chamber 143 has a structure similar to the chamber 113 and interiorly includes a float switch 143a. The chamber 143 is arranged on the lower side of the blood smear preparing apparatus 1 (not shown). As shown in FIG. 6, the container 102 accommodating the diluted solution is connected to the mixed chamber 145 through a valve 134. The valve 134 is connected with a diaphragm pump 136 connected to an air pressure adjustor 135. The mixed chamber 145 is arranged to mix the Giemsa solution or the concentrated stain fluid accommodated in the container 103 and the diluted solution accommodated in the container 102.

The mixed chamber 122 is connected to a waste chamber 163 through a valve 161, and the mixed chamber 145 is connected to the waste chamber 163 through a valve 162. The waste chamber 163 is connected with an air pressure adjustor 164. The waste chamber 163 has a structure similar to the chamber 113 and interiorly include a float switch 163a. The float switch 163a of the waste chamber 163 is arranged to detect whether or not the discharge of the waste solution stored in the waste chamber 163 is accurately carried out. The chamber 113, the chamber 143, and the waste chamber 163 are respectively connected to discharge ports 174, 175, 176 through valves 171, 172, and 173.

The container 104 accommodating the methanol solution is connected at the middle of the supply path of the May-Grunwald solution from the container 101, which accommodates the May-Grunwald solution, to the chamber 113 through a valve 181. The container 104 accommodating the methanol solution is connected at the middle of the supply path of the Giemsa solution from the container 103, which accommodates the Giemsa solution, to the chamber 143 through a valve 182.

In the present embodiment, the container 104 accommodating the methanol solution is connected to the pipette 73a of the first aspirating and discharging unit 73 through a valve 191, as shown in FIG. 6. The valve 191 is connected with the diaphragm pump 193 connected to the air pressure adjustor 192. Thus, the methanol solution for cleaning accommodated in the container 104 can be supplied to the smear sample (slide glass 10) of the first aspirating and discharging unit 73 of the staining section 27 by arranging a path from the container 104 to the pipette 73a of the first aspirating and discharging unit 73 through the valve 191.

The storage section 28 shown in FIG. 2 is arranged to store the cassette 23 in which a stained slide glass 10, which is stained by the staining section 27, is accommodated. The storage section 28 includes a transport belt 28a for transporting the cassette 23.

Figure 7:
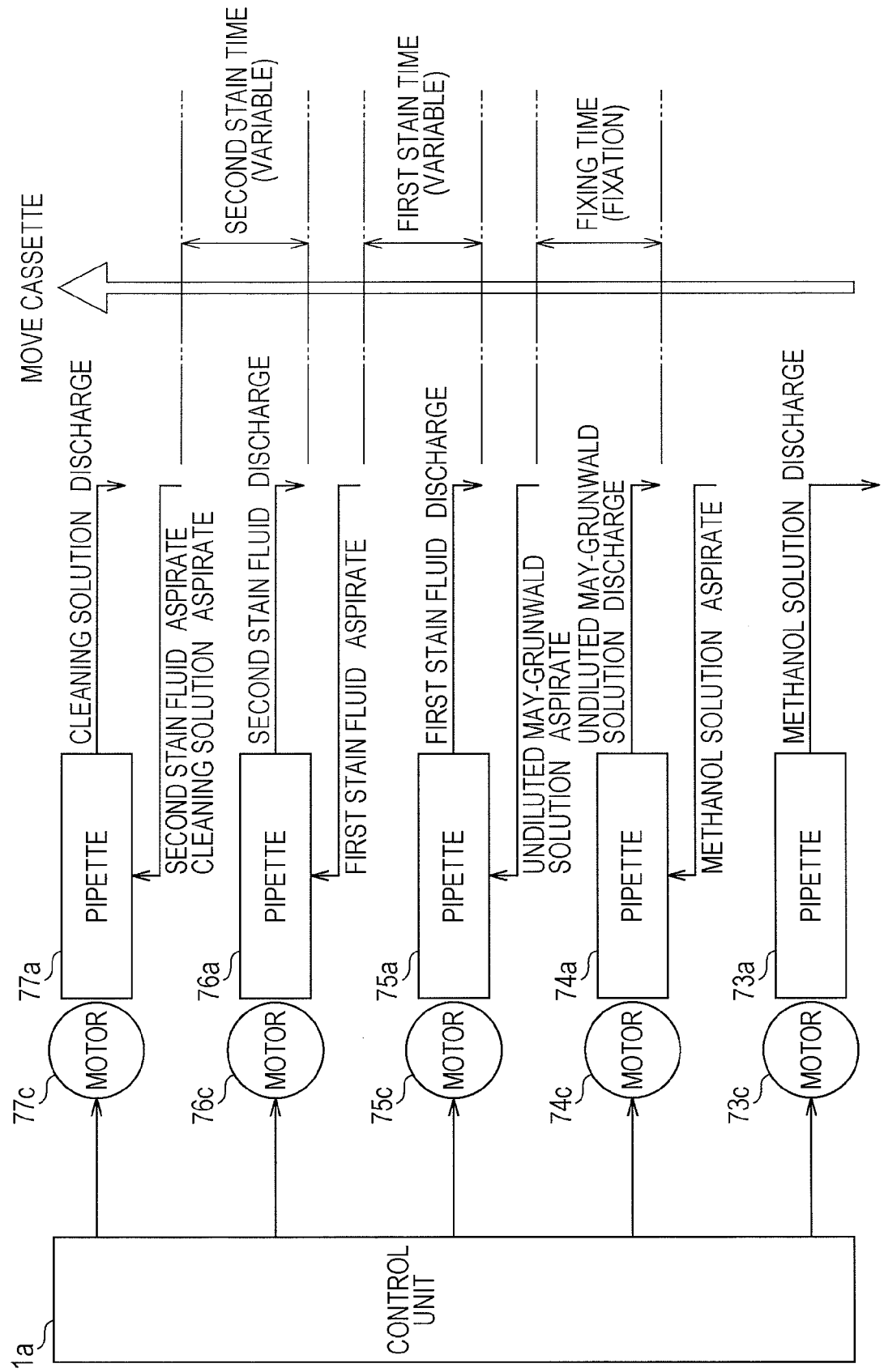
FIG. 7 is a schematic view showing the configuration of the staining section of the blood smear preparing apparatus according to the embodiment.

FIG. 7 is a schematic view showing the configuration of the staining section 27 of the blood smear preparing apparatus 1 according to the present embodiment. The control unit 1a is connected to the motors 73c to 77c arranged in the first to fifth aspirating and discharging units 73 to 77, respectively, and drive controls such motors 73c to 77c. Each motor 73c to 77c is coupled to the pipette 73a to 77a respectively, so that the pipettes 73a to 77a move up and down by the operation of the motors 73c to 77c. Furthermore, the pipettes 73a to 77a perform the aspirating and discharging operation of the fluid by the fluid circuit described above. As described above, the methanol solution, the concentrated May-Grunwald solution, the diluted May-Grunwald solution, the diluted Giemsa solution, and the cleaning solution are respectively supplied to the pipettes 73a to 77a.

According to the above configuration, the staining of the smear sample in the blood smear preparing apparatus 1 is generally proceeded in the following manner. First, the immobilization step of immersing the smeared slide glass 10 in the methanol solution or May-Grunwald solution (undiluted solution) for a predetermined time (hereinafter referred to as "immobilization time") is carried out, and then a first staining step of immersing the smeared and immobilized slide glass 10 in the diluted May-Grunwald solution (hereinafter referred to as "first stain fluid") for a predetermined time (hereinafter referred to as "first staining time") is carried out, a second staining step of immersing the slide glass 10 terminated with the first staining step in the Giemsa diluted solution (hereinafter referred to as "second stain fluid") for a predetermined time (hereinafter referred to as "second staining time") is carried out, and lastly, a cleaning step of cleaning the slide glass 10 is carried out.)

Such blood smear preparing apparatus 1 has a configuration in which the staining condition of the smear sample can be set. The staining condition here is the dilution magnification and the staining time of the concentrated stain fluid. The dilution magnification of the concentrated stain fluid can be set to one of five times, ten times, or twenty times, where the default value is ten times. The average nucleus G value is assumed to change by 30 if the dilution magnification of the concentrated stain fluid is changed one stage. That is, the average nucleus G value is assumed to increase by 30 if the dilution magnification is lowered one stage from ten times to five times or from twenty times to ten times, and the average nucleus G value is assumed to decrease by 30 if the dilution magnification is raised one stage from five times to ten times or from ten times to twenty times. The average nucleus G value is the average value of the G value of the region of the nucleus of the white blood cells in a plurality of blood cell images obtained by imaging the smear sample prepared by the blood smear preparing apparatus 1 with the sample imaging apparatus 3.

The staining time can be set in 11 stages. The staining time that can be set includes the first staining time and the second staining time described above. The setting of the staining time is a combination of the first staining time and the second staining time, and one of the 11 ways of combinations can be set. That is, the first staining time and the second staining time cannot be independently setting changed, and the first staining time and the second staining time are both setting changed. The default value of the staining time is the combination of 5 minutes for the first staining time and 20 minutes for the second staining time, where the first staining time can be setting changed by 0.5 minutes and the second staining time can be setting changed by 2.5 minutes. The lower limit value of the staining time is a combination of 2.5 minutes for the first staining time and 7.5 minutes for the second staining time. The upper limit value of the staining time is a combination of 7.5 minutes for the first staining time and 32.5 minutes for the second staining time. If the staining time is changed one stage, the average nucleus G value is assumed to change by five. For instance, the average nucleus G value increases by five if the default value of "first staining time of 5 minutes and second staining time of 20 minutes" is changed to one stage higher or "first staining time of 5.5 minutes and second staining time of 22.5 minutes", and the average nucleus G value decreases by five if changed to one stage lower or "first staining time of 4.5 minutes and second staining time of 17.5 minutes".

<Configuration of Sample Transport Device>

As shown in FIG. 1, the sample transport device 6 is arranged between the blood smear preparing apparatus 1 and the sample imaging apparatus 3. The sample transport device 6 is arranged to transport the slide glass 10 accommodated in the cassette received from the blood smear preparing apparatus 1 to the sample imaging apparatus 3. As shown in FIG. 1, the sample transport device 6 includes a display unit 6a and a power switch 6b and a cover 6c. The sample transport device 6 is configured to convey out the slide glass 10 to be imaged to the sample imaging apparatus 3 through the convey-out port 6d.

<Configuration of Sample Imaging Apparatus>

Figure 8:
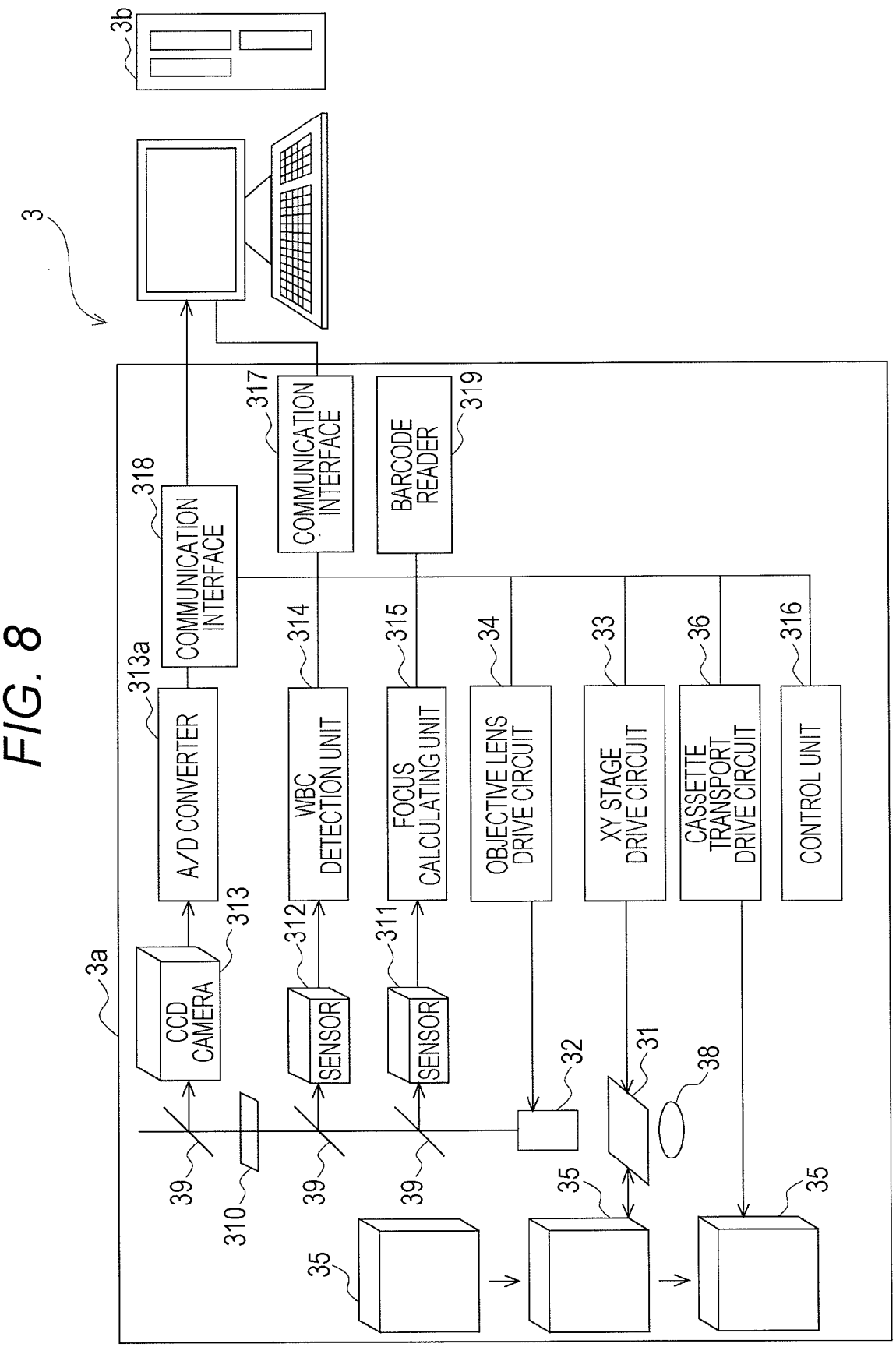
FIG. 8 is a block diagram showing the configuration of the sample imaging apparatus according to the embodiment.

FIG. 8 is a block diagram showing the configuration of the sample imaging apparatus according to the present embodiment. FIG. 8 schematically shows the configuration of the apparatus, where the arrangement of the sensor, the slide cassette, and the like is slightly different from the actual to facilitate the understanding. For instance, in FIG. 8, the sensor for WBC detection and the sensor for autofocus are arranged above and below, but both sensors are actually arranged in substantially the same plane, as shown in FIG. 9.

The sample imaging apparatus 3 includes a microscope unit 3a for imaging an enlarged image of the blood smear sample focused by autofocus, and an image processing unit 3b for processing the imaged image to classify the white blood cells in the blood and counting for every classification of the white blood cells. The sample transport device 6 is arranged near the sample imaging apparatus 3, so that the blood smear sample prepared by the blood smear preparing apparatus 1 is automatically supplied to the microscope unit 3a by the sample transport device 6.

<Configuration of Microscope Unit 3a>

Figure 9:
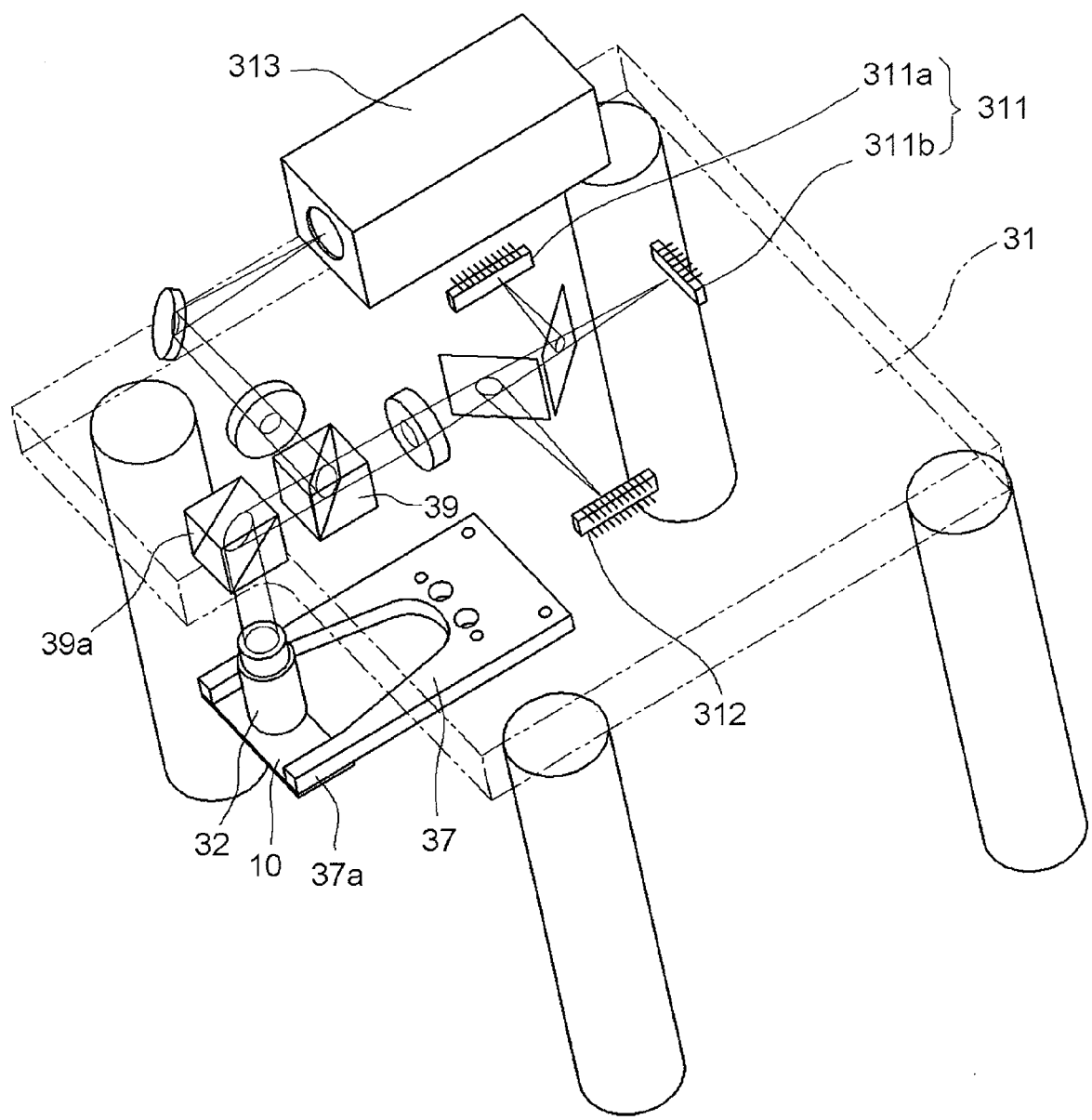
FIG. 9 is a perspective view showing one part of the configuration of the microscope unit of the sample imaging apparatus according to the embodiment.

FIG. 9 is a perspective view showing one part of the configuration of the microscope unit 3a. The microscope unit 3a includes an objective lens 32 configuring one part of the lens system of the microscope for enlarging the image of the blood thinly stretched and applied on the slide glass 10 mounted on the XY stage 31. The XY stage 31 for holding the sample (slide glass 10 having the blood applied on the upper surface) is freely movable forward, backward, leftward, and rightward (X direction and Y direction) by a drive unit (not shown) drive controlled by the XY stage drive circuit 33 (see FIG. 8). The objective lens 32 is freely movable up and down (Z direction) by the drive unit (not shown) drive controlled by the objective lens drive circuit 34.

A plurality of slide glasses 10 is accommodated in the slide cassette 35 in a stacked manner, and such slide cassette 35 is transported by the transport unit (not shown) drive controlled by the cassette transport drive circuit 36. A chuck unit 37 (see FIG. 9) capable of gripping two areas near the ends in the longitudinal direction of the slide glass 10 is arranged on the XY stage 31 in a freely advancing and retreating manner with respect to the slide glass 10 accommodated in the slide cassette 35 stopped at a predetermined position. The slide glass 10 can be gripped by the chuck unit 37, and the chuck unit 37 can be retreated to pull out the slide glass 10 from the slide cassette 35 and arrange it at a predetermined position of the XY stage 31.

A lamp 38 or a light source is arranged on the lower side of the slide glass 10, where the light from the lamp 38 passes the blood on the slide glass 10, and then enters the line sensor 311 for autofocus in which a plurality of pixels is lined in a line, the sensor 312 for white blood cell (WBC) detection in which a plurality of pixels is lined in a line, and the CCD camera 313 through the half mirror 39 and the interference filter 310 arranged on the optical path. The white blood cell detection unit 314 configured by FPGA, ASIC, or the like is connected to the sensor 312 for white blood cell detection, so that the white blood cells are detected by the white blood cell detection unit 314 based on the output signal of the sensor 312. The focus calculating unit 315 configured by FPGA, ASIC, or the like is connected to the sensor 311 for autofocus, so that the information used in the operation of the autofocus is calculated by the focus calculating unit 315 based on the output signal of the sensor 311 and the operation of the autofocus is carried out based on the relevant information.

The microscope unit 3a includes a control unit 316 and communication interfaces 317, 318. The control unit 316 includes a CPU and a memory, where the control unit 316 executes the control program stored in the memory to control each mechanism described above.

The communication interface 317 is data communicably connected to the image processing unit 3b through the communication cable. The communication interface 318 is connected to the CCD camera 313 through the A/D converter 313a, and is also connected to the image processing unit 3b through the communication cable. The image signal (analog signal) output from the CCD camera 313 is A/D converted by the A/D converter 313a, and the image data (digital data) output from the A/D converter 313a is provided to the communication interface 318 and transmitted to the image processing unit 3b.

The microscope unit 3a includes a two-dimensional barcode reader 319. As described above, a two-dimensional barcode indicating the sample ID is printed on the frost part (not shown) of the slide glass 10, and the two-dimensional barcode of the slide glass 10 introduced to the microscope unit 3a is read by the two-dimensional barcode reader 319.

<Configuration of Image Processing Unit 3b>

Figure 10:
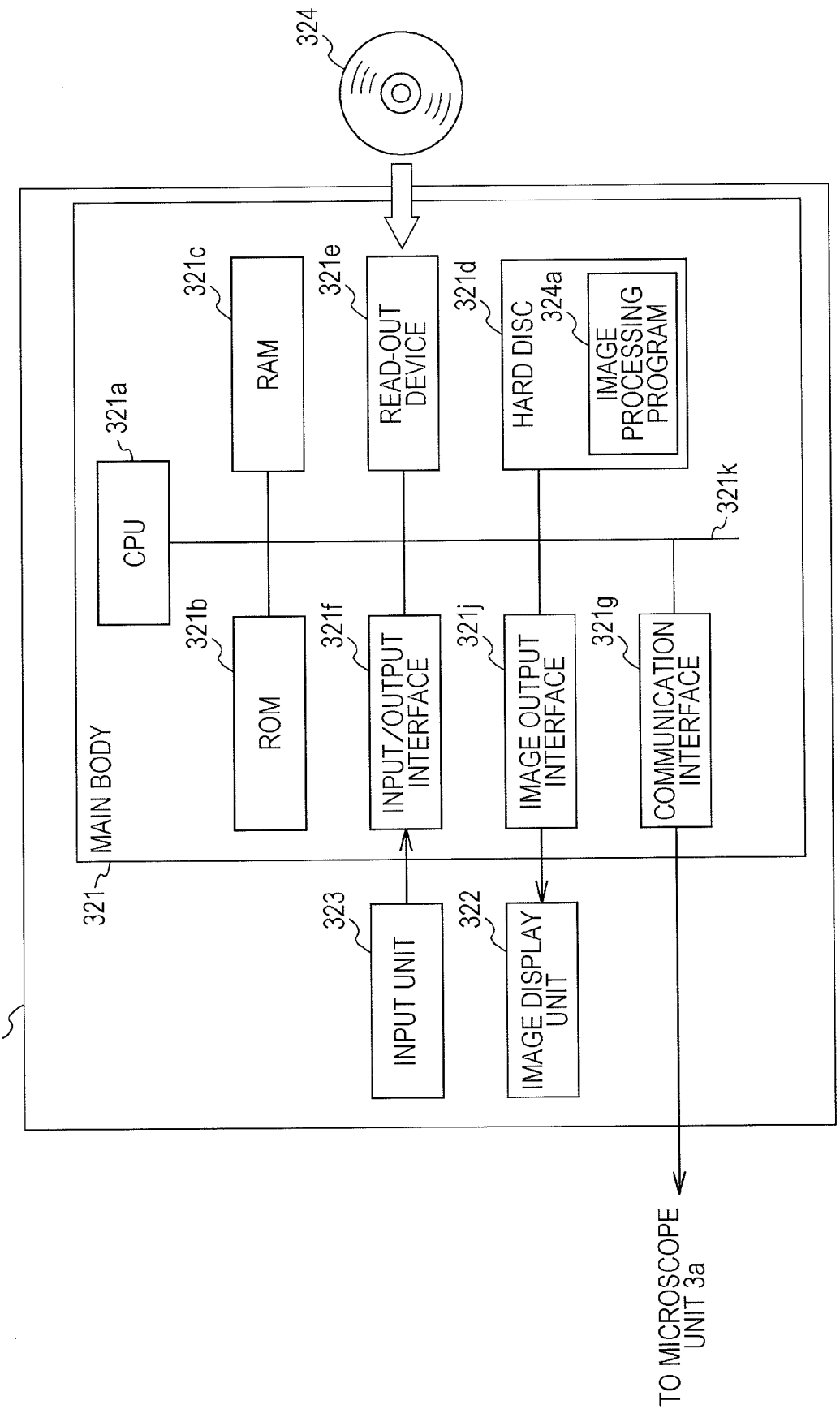
FIG. 10 is a block diagram showing the configuration of the image processing unit of the sample imaging apparatus according to the embodiment.

The configuration of the image processing unit 3b will now be described. FIG. 10 is a block diagram showing the configuration of the image processing unit 3b. The image processing unit 3b is realized by a computer 320. As shown in FIG. 10, the computer 320 includes a main body 321, an image display unit 322, and an input unit 323. The main body 321 includes a CPU 321a, a ROM 321b, a RAM 321c, a hard disc 321d, a read-out device 321e, an input/output interface 321f, a communication interface 321g, and an image output interface 321j, where the CPU 321a, the ROM 321b, the RAM 321c, the hard disc 321d, the read-out device 321e, the input/output interface 321f, the communication interface 321g, and the image output interface 321j are connected by a bus 321k.

The read-out device 321e can read out the computer program 324a for functioning the computer as the image processing unit 3b from the portable recording medium 324, and install the computer program 324a in the hard disc 321d.

The image processing unit 3b stores the image transmitted from the microscope unit 3a in the ROM 321b or the hard disc 321d. The CPU 321a causes the image display unit 322 to display the stored image in accordance with the operation from the user. The CPU 321a also analyzes the stored image and causes the image display unit 322 to display the analysis result in accordance with the operation from the user.

[Operation of Smear Processing System]

The operation of the smear processing system 100 according to the present embodiment will now be described. In the blood smear preparing apparatus 1, the concentrated stain fluid or the diluted solution need to be replaced to a new one if the concentrated stain fluid or the diluted solution is gone or the expiration date for use is overdue. The concentration of the concentrated stain fluid differs depending on the manufacturer. The concentration also differs for every manufacturing lot even if the concentrated stain fluid is manufactured by the same manufacturer. Therefore, the degree of staining tends to differ if the sample is stained under the same staining condition (staining time and dilution magnification) before and after the concentrated stain fluid is replaced. In the blood smear preparing apparatus 1 according to the present embodiment, therefore, the staining conditions are set in the following manner when changing the stain fluid.

Figure 11:
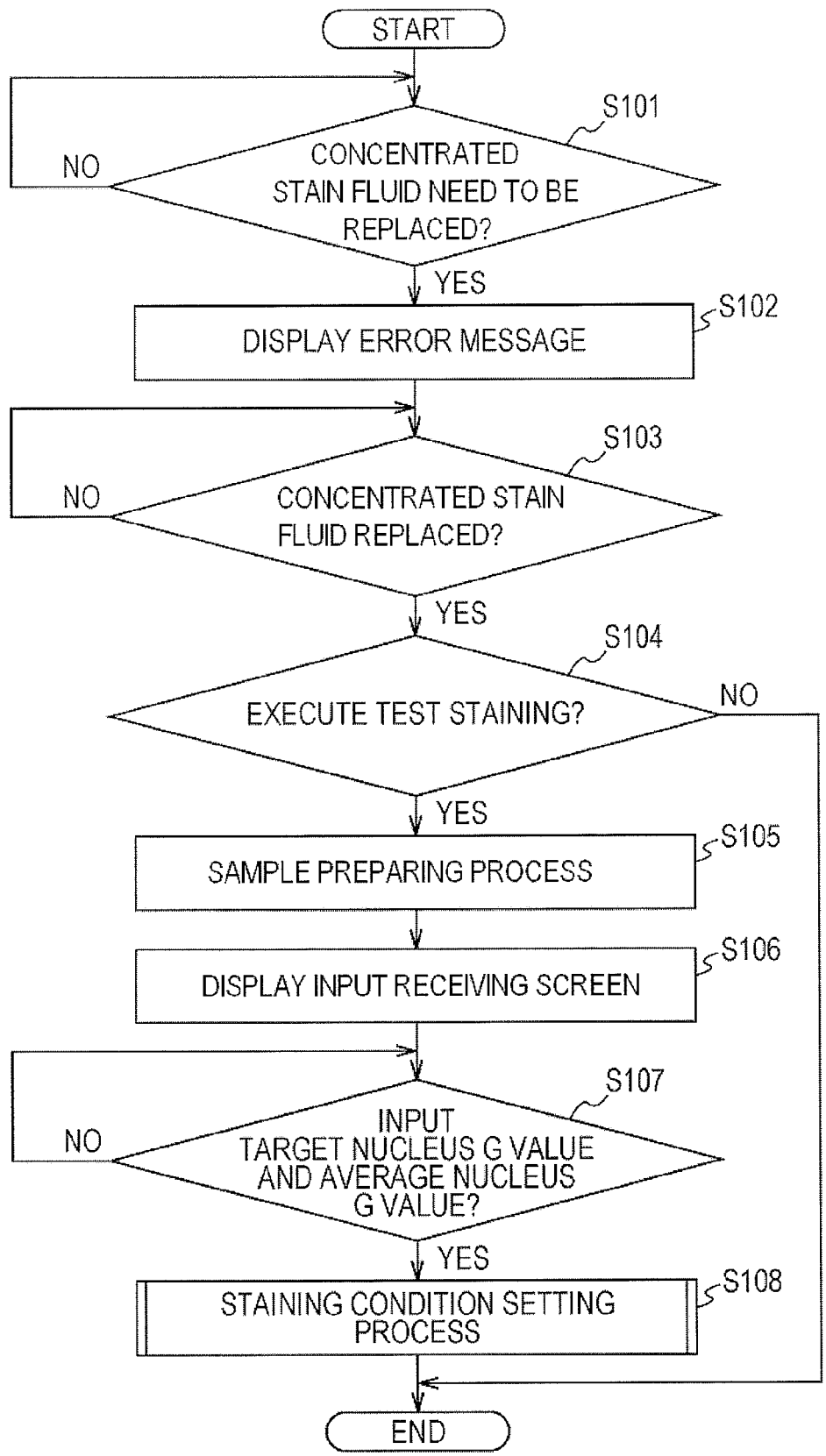
FIG. 11 is a flowchart showing the flow of operation of changing the stain fluid of the blood smear preparing apparatus according to the embodiment.

FIG. 11 is a flowchart showing the flow of operation of changing the concentrated stain fluid of the blood smear preparing apparatus 1 according to the present embodiment. First, the CPU 11 of the control unit 1a of the blood smear preparing apparatus 1 determines whether or not the concentrated stain fluid needs to be replaced (step S101). In this process, determination is made that the May-Grunwald solution needs to be replaced if the supply of the May-Grunwald solution to the chamber 113 is not detected by the float switch 113a even though the valves 111, 112 are opened, and determination is made that the Giemsa solution needs to be replaced if the supply of the Giemsa solution to the chamber 143 is not detected by the float switch 143a even though the valves 141, 142 are opened. The expiration date for use of the May-Grunwald solution and the Giemsa solution are respectively stored in the memory 12 of the control unit 1a, so that the need to replace the concentrated stain fluid can be determined by having the CPU 11 determine whether the date for use has expired. If the concentrated stain fluid does not need to be replaced (NO in step S101), the CPU 11 repeats the process of step S101. If determined that the concentrated stain fluid needs to be replaced (YES in step S101), the CPU 11 displays an error message notifying that the concentrated stain fluid needs to be replaced on the display operation unit 2a (step S102).

The CPU 11 determines whether or not the concentrated stain fluid is replaced (step S103). Determination is made that the concentrated stain fluid is replaced when the error message displayed on the display operation unit 2a is closed by the operator. If the concentrated stain fluid is not replaced (NO in step S103), the CPU 11 repeats the process of step S103. If determined that the concentrated stain fluid is replaced (YES in step S103), the CPU 11 displays the OK button and the NO button on the display operation unit 2a along with the message "Concentrated stain fluid is replaced. Perform test staining?", and determines whether or not the execution of the test staining is instructed (step S104). When the selection of the OK button is detected and the instruction to execute the test staining is made (YES in step S104), the CPU 11 proceeds the process to step S105. When the selection of the NO button is detected, and the instruction not to execute the test staining is made (NO in step S104), the CPU 11 terminates the process. In this case, the setting of the staining conditions is not replaced, and the staining conditions up to now are maintained.

In step S105, the CPU 11 executes the sample preparing process (step S105). In the sample preparing process, the blood is aspirated by the aspirating and dispensing mechanism section 21 from the test tube 51 transported by the transport device 2, and the aspirated blood is dropped on the slide glass 10.

The blood used in the test staining is preferably a fresh blood collected from a healthy person. The fresh blood collected from the healthy person is preferably the blood which measurement value of each measurement item falls within a predetermined range when measured with respect to a plurality of measurement items in the blood cell analyzer and the blood collected within 24 hours.

As hereinafter described, the smear sample stained by the test staining is supplied to the sample imaging apparatus 3, and the average nucleus G value indicating the stain state of the relevant smear sample is obtained. The average nucleus G value is obtained by acquiring the nucleus G value of the neutrophil cells of the white blood cells for a plurality of neutrophil cells, and obtaining the average value of the plurality of nucleus G values. The neutrophil cells are blood cells that occupy 60% of the white blood cells and are always contained in the blood collected from the healthy person, where barely any difference is recognized in the aspect of the neutrophil cells (e.g., easiness to stain) between the samples unless the blood is not degraded. Therefore, a stable average nucleus G value is always obtained only when the fresh blood collected from the healthy person is used in the test staining.

The blood dropped on the slide glass 10 is smeared on the slide glass 10 by the smearing section 22 and then dried. The smear sample obtained in such manner is inserted to the cassette 23, and the test staining is carried out by the staining steps described above in the staining section 27. In the test staining, the staining conditions of the default values are used. That is, the dilution magnification of the concentrated stain fluid is ten times, the first staining time is five minutes, and the second staining time is 20 minutes.

The test staining process will be described in detail. First, when the slide glass 10 that is smeared with the sample is sent to the staining section 27, the immobilization step described above is carried out. In the immobilization step, the methanol solution or the concentrated May-Grunwald solution is discharged into the cassette 23, to which the slide glass 10 is inserted, when the pipette 73a of the first aspirating and discharging unit 73 or the pipette 74a of the second aspirating and discharging unit 74 are operated. The slide glass 10 that is smeared with the sample is immersed in the methanol solution or the concentrated May-Grunwald solution until the immobilization time has elapsed from when the methanol solution or the May-Grunwald solution is supplied into the cassette 23. After the immobilization time has elapsed from when the methanol solution or the May-Grunwald solution is supplied into the cassette 23, the smeared slide glass 10 is lifted up from the slide glass accommodation hole 23a of the cassette 23 by the second aspirating and discharging unit 74, and the air is blown to the smear surface of the slide glass 10 by the fan 78a to dry the fluid component on the smear surface. The immobilization process of the smear sample by the methanol solution is thereby terminated. The time (immobilization time) from when the smeared slide glass 10 is immersed in the methanol solution or the undiluted May-Grunwald solution until the slide glass 10 is lifted up by the second aspirating and discharging unit 74 is about 20 seconds to about 120 seconds. The methanol solution or the May-Grunwald solution inside the cassette 23 is discharged. This is carried out when the methanol solution is aspirated by the pipette 74a if the methanol solution is supplied into the cassette 23, and carried out when the May-Grunwald solution is aspirated by the pipette 75a if the May-Grunwald solution is supplied into the cassette 23. Thereafter, the slide glass 10 is returned to the slide glass accommodation hole 23a of the cassette 23.

The first staining step is then carried out. When supplying the diluted May-Grunwald solution (undiluted solution of first stain fluid) to the pipette 75a of the third aspirating and discharging unit 75, the flow path between the chamber 113 and the diaphragm pump 125 is in the open state by the valve 121 shown in FIG. 6. The interior of the diaphragm pump 125 is depressurized by the air pressure adjustor 124. A constant amount of the May-Grunwald solution of the chamber 113 is aspirated by the diaphragm pump 125. Thereafter, the flow path between the diaphragm pump 125 and the mixed chamber 122 is in the opened state by the valve 121. The interior of the diaphragm pump 125 is pressurized by the air pressure adjustor 124. The May-Grunwald solution of the diaphragm pump 125 is moved to the mixed chamber 122. Thereafter, the flow path between the diaphragm pump 125 and the mixed chamber 122 is in the shielded state by the valve 121. The movement of the May-Grunwald solution of the chamber 113 to the mixed chamber 122 is thereby terminated.

The diluted solution (phosphate buffer solution) of the container 102 is then moved to the mixed chamber 122 to dilute the May-Grunwald solution of the mixed chamber 122. Specifically, the flow path between the container 102 and the diaphragm pump 133 is in the opened state by the valve 131. The interior of the diaphragm pump 133 is depressurized by the air pressure adjustor 132. A constant amount of the diluted solution of the container 102 is aspirated by the diaphragm pump 133. Thereafter, the flow path between the diaphragm pump 133 and the mixed chamber 122 is in the opened state by the valve 131. The interior of the diaphragm pump 133 is pressurized by the air pressure adjustor 132. The diluted solution of the diaphragm pump 133 is moved to the mixed chamber 122. Thereafter, the flow path between the diaphragm pump 133 and the mixed chamber 122 is in the shielded state by the valve 131. The movement of the diluted solution of the container 102 to the mixed chamber 122 is terminated. The first stain fluid of the dilution magnification of ten times, which is the default value, is prepared by controlling the repeating number of times of the constant amount supplying operation of the May-Grunwald solution and the diluted solution to the mixed chamber 122.

After the flow path between the mixed chamber 122 and the diaphragm pump 127 is opened by the valve 123, the interior of the diaphragm pump 127 is depressurized by the air pressure adjustor 126. A constant amount of the first stain fluid of the mixed chamber 122 is thereby aspirated by the diaphragm pump 127. Thereafter, the flow path between the diaphragm pump 127 and the mixed chamber 122 is shielded, and the flow path between the diaphragm pump 127 and the pipette 75a of the third aspirating and discharging unit 75 is opened by the valve 123. The interior of the diaphragm pump 127 is pressurized by the air pressure adjustor 126. The first stain fluid in the diaphragm pump 127 is supplied from the pipette 75a of the third aspirating and discharging unit 75 to the cassette 23 (see FIG. 2).

The slide glass 10 that is smeared with the sample is immersed in the first stain fluid while the cassette 23 is transported by the transport belt 72 and the staining of the sample by the first stain fluid is carried out until the first staining time has elapsed from when the first stain fluid is supplied into the cassette 23. In the test staining, the first staining time is five minutes, which is the default value. After the elapse of the first staining time, the first stain fluid is aspirated by the pipette 76a and the first stain fluid in the cassette 23 is discharged.

The second staining step is then carried out. When supplying the Giemsa diluted solution (undiluted solution of second stain fluid) to the pipette 76a of the fourth aspirating and discharging unit 76 of the staining section 27, the valves 141 and 142 shown in FIG. 6 are first opened from the initial state (all valves are shielded), and the interior of the chamber 143 is depressurized by the air pressure adjustor 147. The Giemsa solution of the container 103 is thereby aspirated to the chamber 143. The float switch 143a installed in the chamber 143 is turned ON with the flow of the Giemsa solution to the chamber 143. The valves 141 and 142 are then shielded, and the depressurization by the air pressure adjustor 147 is released. The movement of the Giemsa solution of the container 103 to the chamber 143 is then terminated.

The Giemsa solution of the chamber 143 is moved to the mixed chamber 145. Specifically, the flow path between the chamber 143 and the diaphragm pump 149 is first opened by the valve 144. The interior of the diaphragm pump 149 is depressurized by the air pressure adjustor 148. A constant amount of Giemsa solution of the chamber 143 is thereby aspirated by the diaphragm pump 149. Thereafter, the flow path between the diaphragm pump 149 and the mixed chamber 145 is in the opened state by the valve 144. The interior of the diaphragm pump 149 is pressurized by the air pressure adjustor 148. The Giemsa solution of the diaphragm pump 149 is moved to the mixed chamber 145. Thereafter, the flow path between the diaphragm pump 149 and the mixed chamber 145 is in the shielded state by the valve 144. The movement of the Giemsa solution of the chamber 143 to the mixed chamber 145 is then terminated.

The diluted solution (phosphate buffer solution) of the container 102 is then moved to the mixed chamber 145 to dilute the Giemsa solution of the mixed chamber 145. Specifically, the flow path between the container 102 and the diaphragm pump 136 is in the opened state by the valve 134. The interior of the diaphragm pump 136 is depressurized by the air pressure adjustor 135. A constant amount of the diluted solution of the container 102 is aspirated by the diaphragm pump 136. Thereafter, the flow path between the diaphragm pump 136 and the mixed chamber 145 is in the opened state by the valve 134. The interior of the diaphragm pump 136 is pressurized by the air pressure adjustor 135. The diluted solution of the diaphragm pump 136 is moved to the mixed chamber 145. Thereafter, the flow path between the diaphragm pump 136 and the mixed chamber 145 is in the shielded state by the valve 134. The movement of the diluted solution of the container 102 to the mixed chamber 145 is terminated. The Giemsa solution is mixed with the diluted solution in the mixed chamber 145 to become the Giemsa diluted solution (second stain fluid). The second stain fluid of the dilution magnification of ten times, which is the default value, is prepared by controlling the repeating number of times of the constant amount supplying operation of the Giemsa solution and the diluted solution to the mixed chamber 145.

After the flow path between the mixed chamber 145 and the diaphragm pump 151 is opened by the valve 146, the interior of the diaphragm pump 151 is depressurized by the air pressure adjustor 150. A constant amount of the second stain fluid of the mixed chamber 145 is thereby aspirated by the diaphragm pump 151. Thereafter, the flow path between the diaphragm pump 151 and the mixed chamber 145 is shielded, and the flow path between the diaphragm pump 151 and the pipette 76a of the fourth aspirating and discharging unit 76 is opened by the valve 146. The interior of the diaphragm pump 151 is pressurized by the air pressure adjustor 150. The Giemsa diluted solution in the diaphragm pump 151 is supplied from the pipette 76a of the fourth aspirating and discharging unit 76 to the cassette 23 (see FIG. 2).

The slide glass 10 is then immersed in the second stain fluid while the cassette 23 is transported by the transport belt 72 and the staining of the sample by the second stain fluid is carried out until the second staining time has elapsed from when the second stain fluid is supplied into the cassette 23. In the test staining, the second staining time is twenty minutes, which is the default value. After the elapse of the second staining time, the second stain fluid is aspirated by the pipette 77a and the second stain fluid in the cassette 23 is discharged.

The cleaning step is then carried out. After the cleaning solution is dispensed to the stain fluid aspirating and dispensing hole 23b of the cassette 23 by the pipette 77a, the stained slide glass 10 aspirated by the pipette 77a is cleaned. The stained slide glass 10 is then dried with the fan 78b. The staining process is thereby completed.

The cassette 23 accommodating the stained slide glass 10 is then sequentially sent to the transport belt 28a of the storage section 28 from the transport 72. The cassette 23 is transported by the transport belt 28a of the storage section 28.

Figure 12:
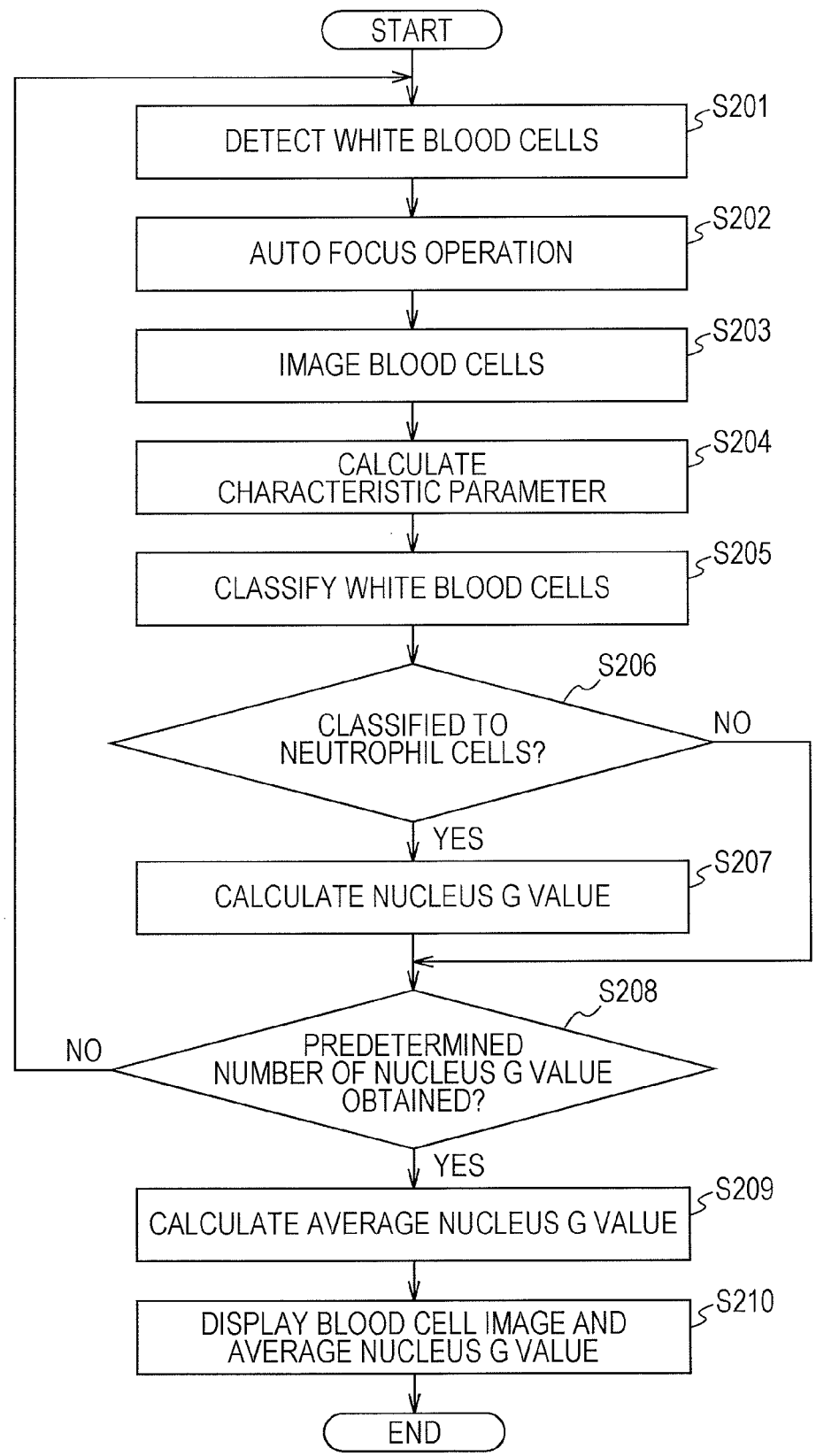
FIG. 12 is a flowchart showing the flow of the blood cell imaging and the image analyzing operation of the sample imaging apparatus according to the embodiment.

After the relevant sample preparing process is completed, the stained smear sample that is prepared is automatically supplied from the blood smear preparing apparatus 1 to the microscope unit 3a by the sample transport device 6. FIG. 12 is a flowchart showing the flow of the blood cell imaging and the image analyzing operation of the sample imaging apparatus 3 according to the present embodiment. The sample imaging apparatus 3 detects the white blood cells in the blood applied to the slide glass 10 with the sensor 312 while moving the slide glass 10 in the X direction and the Y direction with the XY stage 31 (step S201). The control unit 316 then executes the autofocus operation (step S202), and images the stained blood cells (step S203).

The control unit 316 transmits the obtained blood cell image to the image processing unit 3b. The CPU 321a of the image processing unit 3b stores the received blood cell image in the ROM 321b or the hard disc 321d, and calculates various characteristic parameters of the white blood cells based on the blood cell image (step S204). The characteristic parameter includes the area, the number of nucleus, the bumps, the color tone, and the concentration (unevenness) of the nucleus of the white blood cell that can be obtained based on the color signal (G, B, R) of the image, the area, the color tone, and the concentration (unevenness) of the cell cytoplasm of the white blood cells, as well as the area ratio and the concentration ratio of the nucleus and the cell cytoplasm.

The CPU 321a then classifies the type of white blood cells based on the acquired characteristic parameter (step S205). Specifically, for example, the types of white blood cells can be gradually narrowed down by sequentially comparing with the criterion value defined in advance for each parameter with respect to some of the characteristic parameters of the white blood cells. The imaged white blood cells is thus subjected to the classification of mature white blood cells such as lymphocytes, monocytes, acidocytes, basocytes, neutrophil cells (bacillary, lobulated), and the classificaiton of immature white blood cells such as gemmules, young granulocytes, and atypical lymphocytes, and the classification of erythroblasts.

Figure 13:
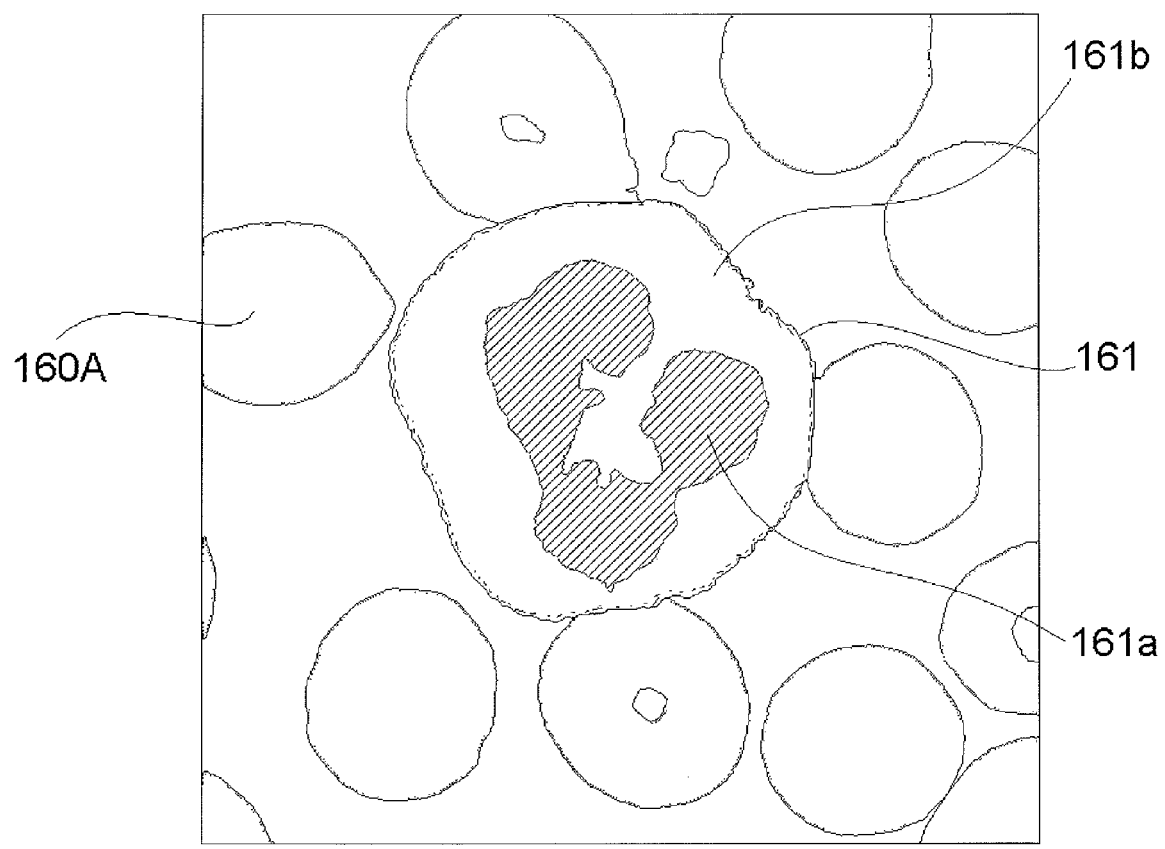
FIG. 13 is a view showing an example of the blood cell image.

FIG. 13 is a view showing an example of the blood cell image. A blood cell image 160A of when the May Giemsa staining is performed includes a blood cell image 161 with a nucleus region 161a and a cytoplasm region 161b. The nucleus region 161a of the blood cell image 160A has different color shades depending on the concentration of the stain fluid and the staining time. The luminance value of the specific color component (green component in the present embodiment) of the nucleus region 161a represents the characteristic of the nucleus region 161a of the blood cell image and shows the stain state of the blood cell.

The image processing unit 3b acquires the stain state information showing the stain state. This will be specifically described below. The CPU 321a determines whether or not the white blood cells in the blood cell image is classified to the neutrophil cells based on the classification of step S205 (step S206). If the white blood cells are classified to the neutrophil cells (YES in step S206), the luminance value (hereinafter referred to as G value) of the green component is acquired of the color components (red: R, green: G, blue: B) of each pixel in the nucleus region of the white blood cells in the blood cell image after the correction, the average value of the G values acquired for all the pixels of the nucleus region is calculated, and the obtained value (nucleus G value) is stored in the RAM 321c (step S207). The CPU 321a then proceeds the process to step S208.

If the white blood cells in the blood cell image are not classified to the nuetrophil cells in step S206 (NO in step S206), the CPU 321a proceeds the process to step S208. In step S208, the CPU 321a determines whether or not the nucleus G value is calculated for a predetermined number (e.g., 100) of blood cell images (step S208). If a predetermined number of nucleus G value is not obtained (NO in step S208), the process returns to step S201, and the processes of steps S201 to S208 are again executed.

If a predetermined number of nucleus G values is obtained (YES in step S208), the CPU 321a calculates the average nucleus G value or the average value of the obtained nucleus G values (step S209). The average nucleus G value becomes the information indicating the stain state of the smear sample stained according to the default staining condition in the staining section 27. The CPU 321a displays the obtained blood cell image and the average nucleus G value on the image display unit 322 (step S210), and terminates the process.

Figure 14:
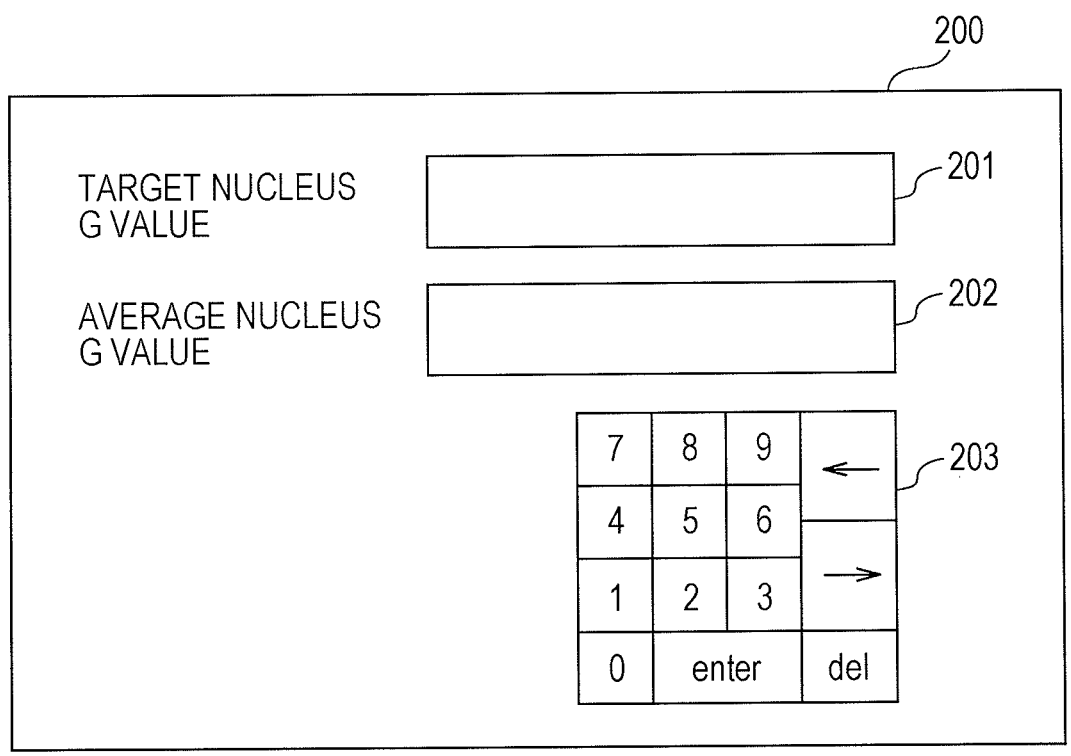
FIG. 14 is a view showing an input receiving screen according to the embodiment.

Returning back to FIG. 11, after the sample preparing process of step S105 is completed, the CPU 11 of the blood smear preparing apparatus 1 displays an input receiving screen for receiving the input of the nucleus G value to become the target (hereinafter referred to as "target nucleus G value") and the average nucleus G value displayed on the image processing unit 3b on the display operation unit 2a (step S106). FIG. 14 is a view showing the input receiving screen. The input receiving screen 200 includes an input area 201 for inputting the target nucleus G value, an input area 202 for inputting the average nucleus G value, and a software key 203 for inputting numbers and the like. The target nucleus G value and the average nucleus G value are respectively a numerical value in the range of 0 to 125. Thus, the numerical value in the range of 0 to 125 can be input to the input areas 201, 202. The user operates the software key 203 displayed on the display operation unit 2a to input the target nucleus G value showing the nucleus G value of the appropriately stained smear sample to the input area 201, and to input the average nucleus G value displayed on the image processing unit 3b to the input area 202, and selects the enter key. The CPU 11 determines whether or not the inputs of the target nucleus G value and the average nucleus G value are received (step S107), and repeats the process of step S107 until input if the target nucleus G value and the average nucleus G value are not input (NO in step S107). If the target nucleus G value and the average nucleus G value are input (YES in step S107), the CPU 11 executes the following staining condition setting process (step S108). If the target nucleus G value is not input and the average nucleus G value is input, the target nucleus G value of default value (e.g., 70) is automatically set.

The nucleus G value indicating the stain state of the appropriately stained smear sample is input for the target nucleus G value. The nucleus G value of the stained smear sample subjected to staining before changing the concentrated stain fluid can be used for such nucleus G value. Such operation is carried out in the following manner.

A plurality of blood cells images of the neutrophil cells obtained by imaging the stained smear sample stained before changing the concentrated stain fluid is stored in the image processing unit 3b of the sample imaging apparatus 3. The user operates the image processing unit 3b to display the stored blood cell images on the image display unit 322, and selects a plurality of blood cell images stained to the desired stain state. The blood cell image selected here is preferably the blood cell image obtained by imaging the smear sample prepared using a fresh blood collected from a healthy person and then stained. The plurality of blood cells images to be selected may be obtained from one stained smear sample or may be respectively obtained from different stained smear samples, and are not particularly limited.

The user instructs the image processing unit 3b to execute the process (process of step S207 of FIG. 12) for obtaining the average nucleus G value of the plurality of selected blood cell images. The image processing unit 3b obtains the nucleus G value for each of the plurality of blood cell images, and displays the average value thereof on the image display unit 322. The user inputs the displayed value in the input receiving screen as the target nucleus G value.

The staining condition capable of realizing substantially the same stain state as the desired stain state obtained before changing the concentrated stain fluid can be set by inputting the target nucleus G value and setting the staining conditions.

Figure 15A:
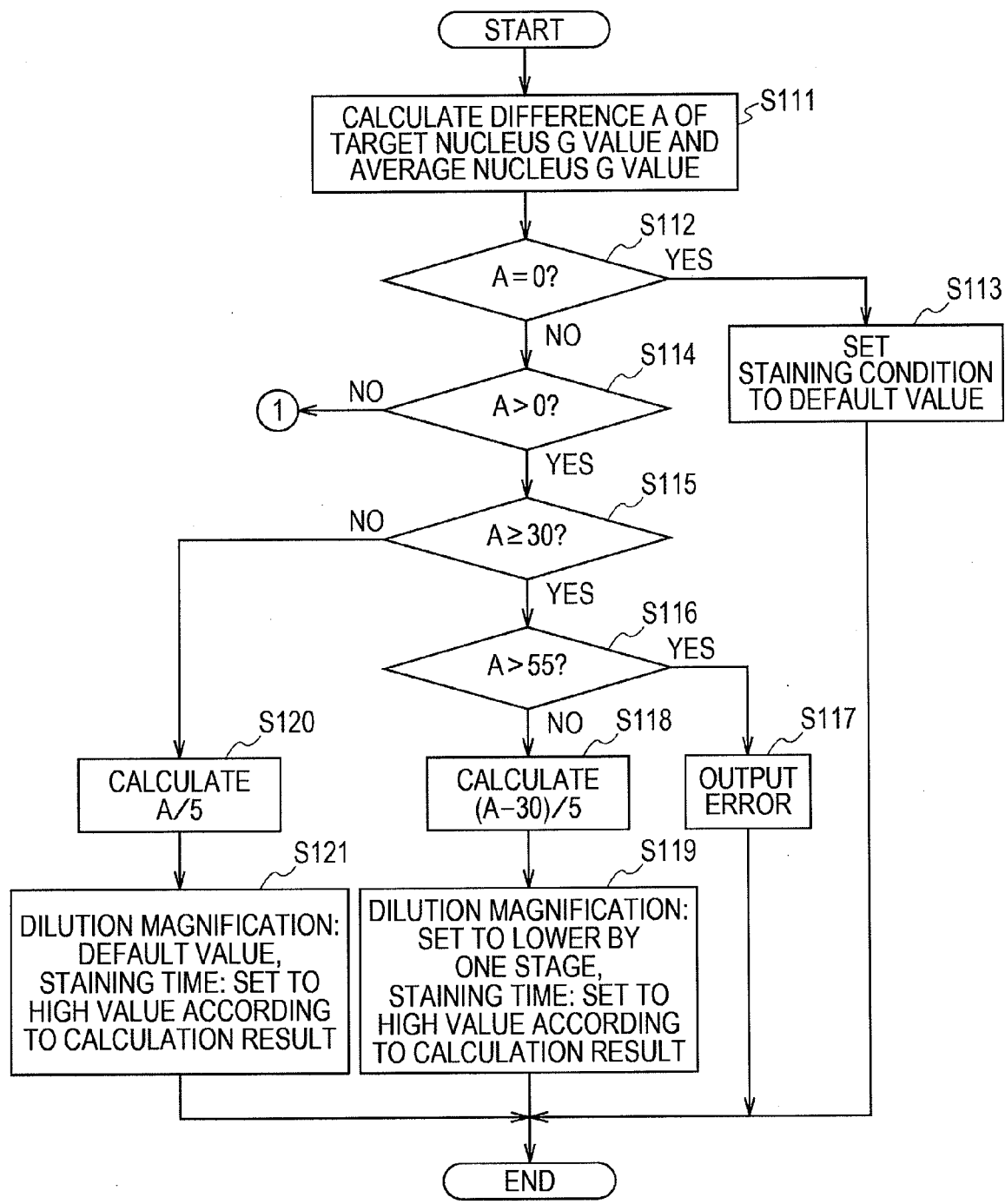
FIG. 15A is a flowchart showing the flow of the staining condition setting process of the blood smear preparing apparatus according to the embodiment (first half)
Figure 15B:
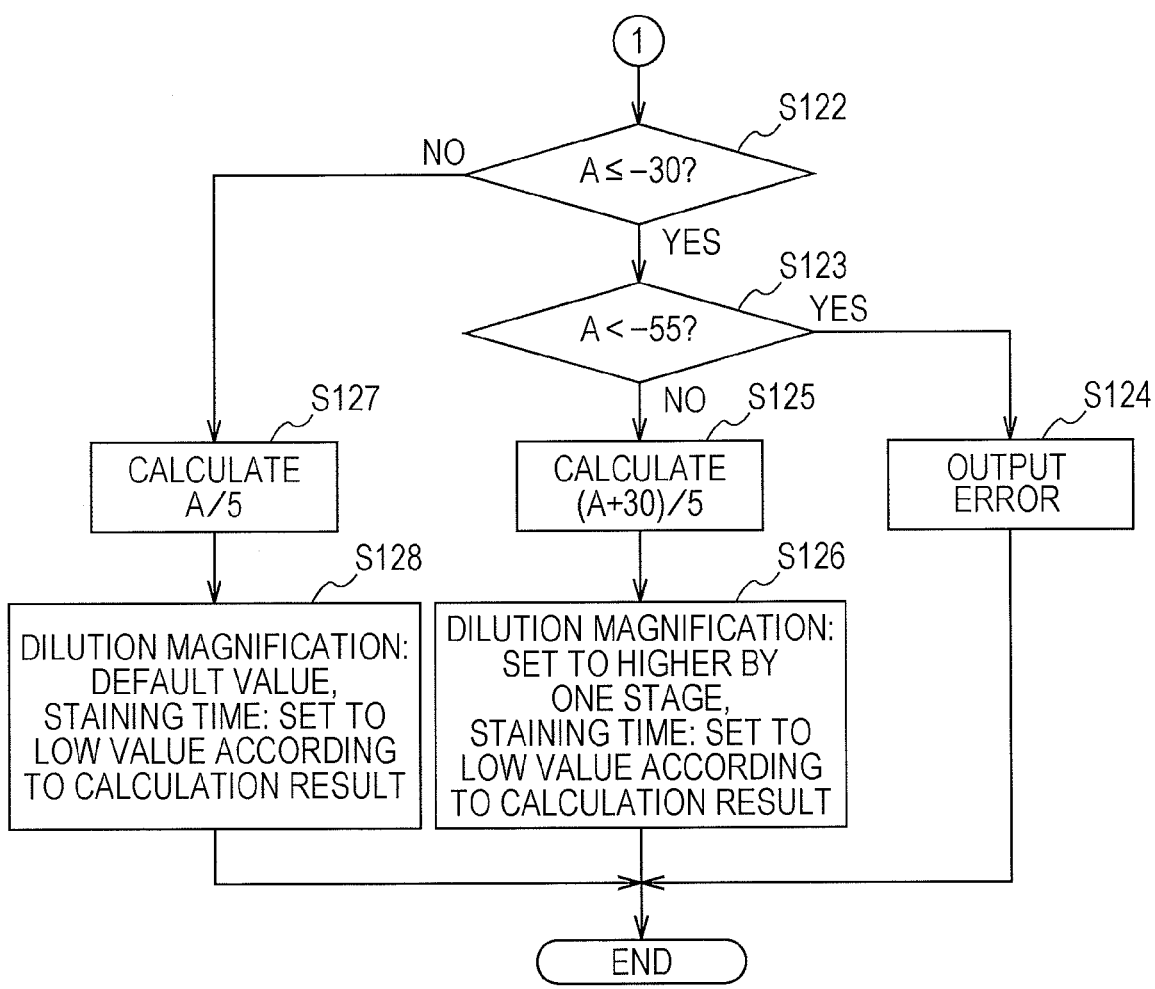
FIG. 15B is a flowchart showing the flow of the staining condition setting process of the blood smear preparing apparatus according to the embodiment (second half)

FIG. 15A and FIG. 15B are flowcharts showing the flow of the staining condition setting process. The CPU 11 performs a calculation to subtract the average nucleus G value from the input target nucleus G value to calculate a difference A (step S111). The CPU 11 then determines whether or not the difference A is zero (step S112), and sets the dilution magnification and the staining time (first staining time and second staining time), which are the staining conditions, to default values (step S113) if the difference A is zero (YES in step S112), and returns the process to the call-out address of the staining condition setting process in the main routine.

If the difference A is not zero (NO in step S112), the CPU 11 determines whether or not the difference A is greater than zero (positive) (step S114), and determines whether or not the difference A is greater than or equal to 30 (step S115) if the difference A is positive (YES in step S114). If the difference A is greater than or equal to 30 (YES in step S115), the CPU 11 determines whether or not the difference A is greater than 55 (step S116). If the difference A is greater than 55 (YES in step S116), abnormality that cannot be handled by changing the staining condition is assumed to have occurred, and hence the CPU 11 causes the display operation unit 2a to display the error message (step S117) and returns the process to the call-out address of the staining condition setting process in the main routine.

If the difference is greater than or equal to 30 and smaller than or equal to 55 (NO in step S116), the CPU 11 performs a calculation of subtracting 30 from the difference A and dividing the result thereof by five (step S118). If there is a remained in the process of step S118, such remained is cut off. That is, an integer in the range of 0 to 5 is obtained in the process of step S118. The CPU 11 then sets the staining conditions (step S119). In the process of step S119, the dilution magnification is lowered by one stage and the staining time is raised by the number obtained in the process of step S118. That is, the dilution magnification is set to 5 times, which is one stage lower than the default value of ten times, and the staining time is set to a value higher than the default value of five minutes for the first staining time and twenty minutes for the second staining time by the number obtained in the process of step S118, and the set values are stored in the memory 12. After the setting of the staining conditions is completed, the CPU 11 returns the process to the call-out address of the staining condition setting process in the main routine.

If the difference A is smaller than 30 in step S115 (NO in step S115), the CPU 11 performs a calculation of dividing the difference A by five (step S120). If there is a remained in the process of step S120, such remained is cut off. That is, an integer in the range of 0 to 5 is obtained in the process of step S120. The CPU 11 then sets the staining conditions (step S121). In the process of step S121, the dilution magnification is not changed and the staining time is raised by the number obtained in the process of step S120. That is, the dilution magnification is set to the default value of ten times, and the staining time is set to a value higher than the default value of five minutes for the first staining time and twenty minutes for the second staining time by the number obtained in the process of step S120, and the set values are stored in the memory 12. After the setting of the staining conditions is completed, the CPU 11 returns the process to the call-out address of the staining condition setting process in the main routine.

If the difference A is negative in step S114 (NO in step S114), the CPU 11 determines whether or not the difference A is smaller than or equal to −30 (step S122). If the difference A is smaller than or equal to −30 (YES in step S122), the CPU 11 determines whether or not the difference A is smaller than −55 (step S123). If the difference A is smaller than −55 (YES in step S123), abnormality that cannot be handled by changing the staining condition is assumed to have occurred, and hence the CPU 11 causes the display operation unit 2a to display the error message (step S124) and returns the process to the call-out address of the staining condition setting process in the main routine.

If the difference is smaller than or equal to −30 and greater than or equal to −55 (NO in step S123), the CPU 11 performs a calculation of adding 30 to the difference A and dividing the result thereof by five (step S125). If there is a remained in the process of step S125, such remained is cut off. That is, an integer in the range of 0 to −5 is obtained in the process of step S125. The CPU 11 then sets the staining conditions (step S126). In the process of step S126, the dilution magnification is raised by one stage and the staining time is lowered by the number obtained in the process of step S125. That is, the dilution magnification is set to twenty times, which is one stage higher than the default value of ten times, and the staining time is set to a value lower (value lower by one stage if −1) than the default value of five minutes for the first staining time and twenty minutes for the second staining time by the number obtained in the process of step S125, and the set values are stored in the memory 12. After the setting of the staining conditions is completed, the CPU 11 returns the process to the call-out address of the staining condition setting process in the main routine.

If the difference A is smaller than −30 in step S122 (NO in step S122), the CPU 11 performs a calculation of dividing the difference A by five (step S127). If there is a remained in the process of step S127, such remained is cut off. That is, an integer in the range of 0 to −5 is obtained in the process of step S127. The CPU 11 then sets the staining conditions (step S128). In the process of step S128, the dilution magnification is not changed and the staining time is lowered by the number obtained in the process of step S127. That is, the dilution magnification is set to the default value of ten times, and the staining time is set to a value lower (value lower by one stage if −1) than the default value of five minutes for the first staining time and twenty minutes for the second staining time by the number obtained in the process of step S127, and the set values are stored in the memory 12. After the setting of the staining conditions is completed, the CPU 11 returns the process to the call-out address of the staining condition setting process in the main routine.

After the staining condition setting process is terminated, the CPU 11 terminates the process.

After the staining conditions are set, the set values are stored in the memory 12 of the control unit 1a, and used in the subsequent staining process of the smear sample.

Figure 16:
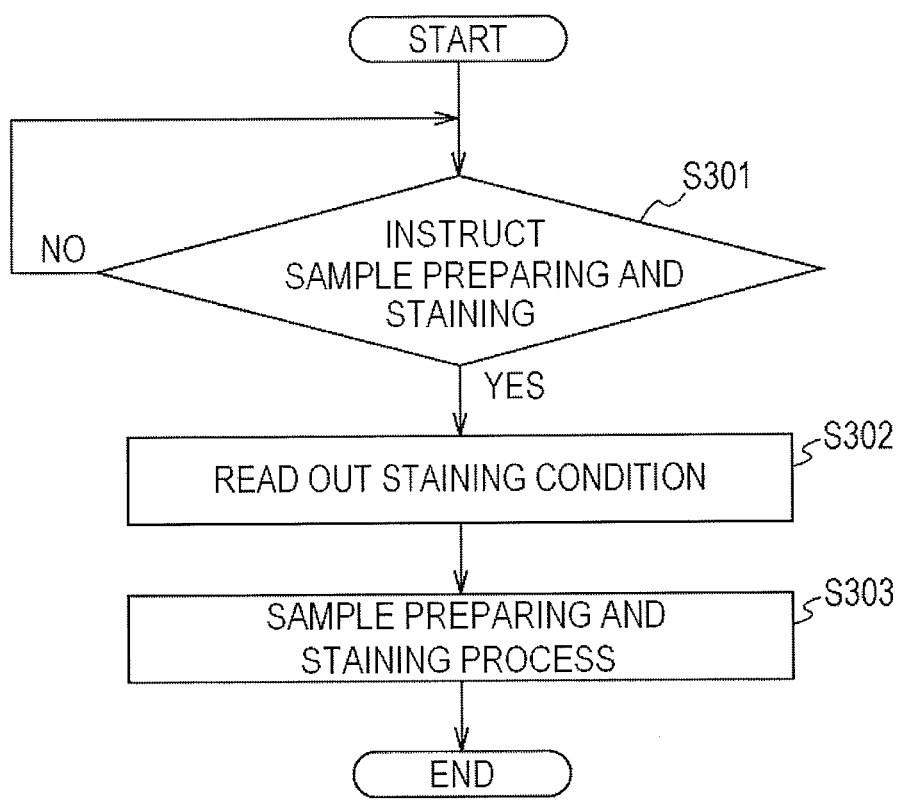
FIG. 16 is a flowchart showing the flow of the smear sample preparing and staining process after changing the concentrated stain fluid by the blood smear preparing apparatus according to the present invention.

FIG. 16 is a flowchart showing the flow of the smear sample preparing and staining process after changing the concentrated stain fluid by the blood smear preparing apparatus 1 according to the present embodiment. The CPU 11 determines whether or not the preparing and the staining of the smear sample are instructed from the user (step S301). If not instructed (NO in step S301), the process of step S301 is repeated until instruction is made. The CPU 11 determines that the instruction is made when the test tube 51 accommodating the blood is set in the transport device 2 by the user, and the preparing and the staining of the smear sample are instructed from the display operation unit 2a (YES in step S301), and reads out the set values of the staining conditions stored in the memory 12 (step S302). The CPU 11 then executes the sample preparing and staining process (step S303). In the sample preparing process, the blood is aspirated by the aspirating and dispensing mechanism section 21 from the test tube 51 transported by the transport device 2, and the aspirated blood is dropped on the slide glass 10. The blood dropped on the slide glass 10 is smeared on the slide glass 10 by the smearing section 22 and then dried. The smear sample obtained in such manner is inserted to the cassette 23, and the staining is carried out by the staining section 27. In the staining process, the smear sample is stained according to the set values of the staining conditions read from the memory 12 in step S302 using the undiluted solution of the stain fluid same as the concentrated stain fluid used in the test staining. Specifically, the new concentrated stain fluid that was replaced is diluted according to the set dilution magnification to prepare first and second stain fluids. The smear sample is subjected to staining by the first stain fluid in the set first staining time, and to staining by the second stain fluid in the set second staining time. After the smear sample preparing and the staining process is terminated, the CPU 11 terminates the process.

According to such configuration, the operator inputs the target nucleus G value and the average nucleus G value, and can set the staining conditions with which the nucleus G value close to the target nucleus G value can be expected to be obtained according to the difference A of the input target nucleus G value and the average nucleus G value. Therefore, the operator can easily set the appropriate staining conditions. Skilled training is not required to set the staining conditions, and the setting of the staining conditions can be prevented from varying for every operator.

Furthermore, the staining state can be greatly changed by changing the dilution magnification and the staining state can be finely tuned by changing the staining time by individually setting the dilution magnification and the staining time. Therefore, the operator can finely and accurately set the desired staining conditions.

Other Embodiments

In the embodiment described above, the average nucleus G value displayed on the image processing unit 3b is input to the blood smear preparing apparatus 1 by the user, but this is not the sole case. The blood smear preparing apparatus 1 and the sample imaging apparatus 3 may be communicably connected, the average nucleus G value may be obtained by the sample imaging apparatus is provided to the blood smear preparing apparatus by communication, and the blood smear preparing apparatus 1 automatically may set the staining condition using the average nucleus G value.

In the embodiment described above, a configuration of performing the test staining and the setting of the staining conditions when changing the undiluted solution of the stain fluid has been described, but is not limited thereto. The test staining and the setting of the staining conditions may be performed in an arbitrary period, and for example, the test staining and the setting of the staining conditions may be carried out in the maintenance task of the blood smear preparing apparatus 1.

In the embodiment described above, a configuration of setting the staining conditions of the blood smear preparing apparatus 1 using the average nucleus G value related to the G value of the region of the nucleus of the blood cell image has been described, but is not limited thereto. The value (average nucleus B value or average nucleus R value) obtained by averaging the B values or the R values of the region of the nucleus of the blood cell image for every sample may be obtained instead of the average nucleus G value, and the staining conditions may be set using the average nucleus B value or the average nucleus R value. The blood cell image of the density image may be obtained, and the staining conditions may be set using the average value of the brightness (luminance) of the region of the nucleus of the blood cell image. The staining conditions may be set using the nucleus G value (or the nucleus B value or the nucleus R value) calculated from one blood cell image instead of the average value of the nucleus G value calculated from each of the plurality of blood cell images, or the blood cell image or one density image may be obtained and the staining conditions may be set using the average value of the brightness of the region of the nucleus of the blood cell image. Furthermore, the G value (or B value, R value, or brightness of density image) of one pixel in the region of the nucleus of the blood cell image may be used as a representative value, and the staining conditions may be set using such value.

In the embodiment described above, the input of the target nucleus G value and the average nucleus G value is received, and the staining conditions are set based on the input target nucleus G value and the average nucleus G value, but this is not the sole case. The target nucleus G value may be stored as a fixed value, the input of only the average nucleus G value may be requested, and the staining conditions may be set based on the input average nucleus G value and the stored target nucleus G value. The user may set the target nucleus G value, the input of the target nucleus G value may not be requested when requesting for the input of the average nucleus G value, and the staining conditions may be set using the input average nucleus G value and the target nucleus G value stored as the set value.

In the embodiment described above, the dilution magnification is determined by the magnitude of the difference A between the target nucleus G value and the average nucleus G value, and the staining time is determined by performing a predetermined calculation using the difference A, but this is not the sole case. The set value may be changed from a default value by the amount of change of the staining condition corresponding to the difference A with reference to a table storing the relationship of the difference A, and the amount of change from the default value of the staining condition (dilution magnification, first staining time, and second staining time).

In the embodiment described above, the staining conditions are reset to the default setting uniformly at the time of test staining, but this is not the sole case. For instance, the test staining may be carried out based on the setting of immediately before the test staining.

In the embodiment described above, the configuration in which the blood smear preparing apparatus for preparing the smear sample sets the staining conditions has been described, but this is not the sole case. The smear staining apparatus, which does not have a function of preparing a smear sample but has a function of staining the smear sample, may receive the input of the target nucleus G value and the average nucleus G value, and set the staining conditions based on the input target nucleus G value and the average nucleus G value.

INDUSTRIAL APPLICABILITY

The smear staining apparatus, the smear preparing apparatus, the smear processing system, and the method of determining the staining conditions of the present invention are useful as a smear staining apparatus for staining a smear sample in which a sample such as blood is smeared on a slide glass, a smear preparing apparatus and a smear processing system, as well, as a method of determining the staining conditions in the staining of the smear sample.

The invention claimed is:
1. A smear staining apparatus comprising:
a staining section comprising a stain fluid preparing unit for preparing a stain fluid by mixing a concentrated stain fluid and a diluting fluid and a supplying unit for supplying a smear sample with the prepared stain fluid to stain the smear sample; and
a controller,
wherein the controller:
receives information indicating a density of stain of a smear sample which is stained according to a first staining condition by the staining section, the information being calculated from a plurality of color densities of a nucleus of a plurality of white blood cells in the smear sample stained according to the first condition;
determines a second staining condition on the basis of the information and a target value which defines a predetermined targeted density of the stain, and
controls the staining section such that the stain fluid is prepared under the second staining condition, and
wherein the determining of the second staining condition comprises:
adjusting a mixing ratio of the first staining condition to increase the proportion of the concentrated stain fluid when the density of stain of the smear sample indicated by the information is lighter than the predetermined targeted density, and
adjusting the mixing ratio of the first staining condition to decrease the proportion of the concentrated stain fluid when the density of stain of the smear sample indicated by the information is darker than the predetermined targeted density.
2. The smear staining apparatus according to claim 1, wherein the information is a numerical value indicating the stain state of the smear sample, and wherein the controller:
compares the information and the target value, and determines the second staining condition based on the comparison result.

3. The smear staining apparatus according to claim 1, wherein the controller causes the staining section to stain a smear sample according to the second staining condition after the second staining condition is determined.

4. The smear staining apparatus according to claim 1, wherein the stain fluid preparing unit comprises:
a mixing chamber for mixing the concentrated stain fluid and the diluting fluid;
a first supplying unit for supplying the concentrated stain fluid to the mixing chamber; and
a second supplying unit for supplying the diluting fluid to the mixing chamber, and
wherein the controller controls the first supplying unit and the second supplying unit respectively so that a first quantity of the concentrated stain fluid and a second quantity of the diluting fluid are supplied to the mixing chamber, the first and second quantities being determined according to the mixing ratio.

5. The smear staining apparatus according to claim 4, wherein the first supplying unit and the second supplying unit respectively comprise a diaphragm pump for supplying a predetermined amount of fluid to the mixing chamber in one operation, and
wherein the controller controls the number of operations of each diaphragm pump according to the mixing ratio.

6. The smear staining apparatus according to claim 1, wherein the staining section comprises:
a transport unit for transporting a container accommodating the smear sample; and
a discharging and aspirating unit for discharging the stain fluid into the container transported by the transport unit and aspirating the stain fluid from the inside of the container, and
wherein the controller controls the discharging and aspirating unit so as to discharge the stain fluid into the container transported by the transport unit and to aspirate the stain fluid from the inside of the container after elapse of the determined staining time from when the stain fluid is discharged.

7. The smear staining apparatus according to claim 6, wherein the discharging and aspirating unit comprises:
a first pipette for discharging the stain fluid to the container at a first position on a transport path of the transport unit, and
a second pipette for aspirating the stain fluid in the container at a second position on a downstream side of the first position on the transport path of the transport unit, and
wherein the controller controls:
the first pipette to discharge the stain fluid into the container of the first position,
the transport unit to transport the container from the first position to the second position; and
the second pipette to aspirate the stain fluid from the container at the second position after elapse of the staining time from the discharge of the stain fluid by the first pipette.

8. The smear staining apparatus according to claim 1, wherein the controller:
determines the second staining condition by adjusting the mixing ratio of the concentrated stain fluid and the diluting fluid and a staining time for staining the smear sample using the prepared stain fluid of the first staining condition based on the information and the target value; and
causes the staining section to prepare the stain fluid by mixing the concentrated stain fluid and the diluting fluid according to the adjusted mixing ratio and to stain the smear sample according to the determined staining time using the prepared stain fluid.

9. The smear staining apparatus according to claim 8, wherein the information is a numerical value indicating the plurality of color densities of the nucleus of the plurality of white blood cells in the density of the stain of the smear sample; and the controller compares the information and the target value, adjusts the mixing ratio when a difference between the information and the target value is greater than a predetermined value, and adjusts the staining time when the difference is smaller than the predetermined value.

10. The smear staining apparatus according to claim 9, wherein the controller issues an error notification when the difference is greater than a predetermined range.

11. The smear staining apparatus according to claim 1, further comprising a display unit, wherein the controller causes the display unit to display a screen for inputting information.

12. The smear staining apparatus according to claim 11, wherein the controller causes the staining section to stain the smear sample according to the first staining condition in an operation of staining a smear sample, the operation being initially operated after replacement of the concentrated stain fluid, and
wherein the controller causes the display unit to display the screen after the smear sample is stained according to the first staining condition.

13. The smear staining apparatus according to claim 1, wherein the controller comprises a storage unit for storing the first staining condition, and
wherein the controller determines the second staining condition based on the information, the target value, and the first staining condition stored in the storage unit.

14. The smear staining apparatus according to claim 13 further comprising a display unit, wherein the controller:
causes the display unit to display a screen for receiving an instruction to perform a test staining when the concentrated stain fluid is replaced, the test staining is performed according to the first staining condition,
reads out the first staining condition from the storage unit automatically when the instruction is received, and
causes the staining section to stain a smear sample according to the first staining condition.

15. The smear staining apparatus according to claim 1, wherein the staining section is configured to stain the smear sample using two types of stain fluids.

16. The smear staining apparatus according to claim 1, wherein the smear sample is a sample obtained by smearing a blood sample on a slide glass.

17. A smear processing system comprising:
the smear staining apparatus according to claim 1; and
a smear imaging apparatus for imaging the smear sample stained by the smear staining apparatus to acquire an image, analyze the obtained image, and output information of the smear sample.

18. A smear preparing apparatus comprising:
a smear preparing section for preparing a smear sample by smearing a sample on a slide glass;
a staining section comprising a stain fluid preparing unit for preparing a stain fluid by mixing a concentrated stain fluid and a diluting fluid and a supplying unit for supplying a smear sample with the prepared stain fluid to stain the smear sample; and a controller, wherein the controller:
receives information indicating a density of a stain state on a smear sample which is stained according to a first staining condition by the staining section, the information being calculated from a plurality of color densities of a nucleus of a plurality of white blood cells in the smear sample stained according to the first condition;

determines a second staining condition on the basis of the information and a target value which defines a predetermined targeted density of the stain, and controls the staining section such that the stain fluid is prepared under the second staining condition, and wherein the determining of the second staining condition comprises:
adjusting a mixing ratio of the first staining condition to increase the proportion of the concentrated stain fluid when the density of the stain state of the smear sample indicated by the information is lighter than the predetermined targeted density, and adjusting the mixing ratio of the first staining condition to decrease the proportion of the concentrated stain fluid when the density of the stain state of the smear sample indicated by the information is darker than the predetermined targeted density.

19. A method of determining a staining condition comprising:
mixing a concentrated stain fluid and a diluting fluid to prepare a stain fluid and staining a smear sample with the prepared stain fluid by a staining apparatus according to a first staining condition;

acquiring information indicating a density of a stain of the smear sample, which is calculated from a plurality of color densities of a nucleus of a plurality of white blood cells in the smear sample stained by the staining apparatus according to the first staining condition from a smear imaging apparatus for imaging the stained smear sample and outputting the information; and determining a second staining condition of the staining apparatus based on the acquired information and a target value which defines a predetermined targeted density of the stain, wherein the determining of the second staining condition comprises:
adjusting a mixing ratio of the first staining condition to increase the proportion of the concentrated stain fluid when the density of the stain of the smear sample indicated by the acquired information is lighter than the predetermined targeted density, and adjusting the mixing ratio of the first staining condition to decrease the proportion of the concentrated stain fluid when the density of the stain of the smear sample indicated by the acquired information is darker than the predetermined targeted density.

20. The method of determining a staining condition according to claim 19, further comprising: receiving the target value input by a user.

21. A smear staining apparatus comprising:
a staining section comprising:
a stain fluid preparing unit configured to prepare a stain fluid by mixing a concentrated stain fluid and a diluting fluid; and a supplying unit configured to supply a smear sample with the prepared stain fluid to stain the smear sample; and a controller configured to:
control the staining section to prepare the stain fluid according to a test staining condition in order calibrate a staining condition;

receive information corresponding to a density of stain of a smear sample stained according to the test staining condition by the staining section, the information corresponding to a plurality of color densities of a nucleus of a plurality of white blood cells in the smear sample stained according to the test condition;

determine a second staining condition based on the received information and a target value corresponding to a target density of the stain, and control the staining section to prepare the stain fluid according to the second staining condition.

22. The smear staining apparatus according to claim 21, wherein the controller is further configured to determine the second staining by:
adjusting a mixing ratio of the test staining condition to increase the proportion of the concentrated stain fluid when the density of the stain of the smear sample indicated by the received information is lighter than the target density, adjusting the mixing ratio of the test staining condition to decrease the proportion of the concentrated stain fluid when the density of the stain of the smear sample indicated by the received information is darker than the target density, and not adjusting the mixing ratio of the test staining condition when the density of the stain of the smear sample indicated by the received information is within a predetermined range of the target density.

23. The smear staining apparatus according to claim 21, further comprising:
a smear imaging apparatus configured:
to obtain an image of the smear sample stained according to the test staining condition, and to calculate the received information corresponding to the density of stain of the smear sample stained according to the test staining condition based on the obtained image.

24. The smear staining apparatus according to claim 21, wherein the smear sample stained according to the test staining condition comprises fresh blood from a healthy person.

* * * * *